(12) United States Patent
Freimoser-Grundschober et al.

(10) Patent No.: US 9,994,610 B2
(45) Date of Patent: Jun. 12, 2018

(54) SEPARATION METHOD FOR FUCOSYLATED ANTIBODIES

(71) Applicant: Roche Glycart AG, Schlieren (CH)

(72) Inventors: Anne Freimoser-Grundschober, Zurich (CH); Christiane Jaeger, Niederweningen (CH); Peter Sondermann, Stockdorf (DE); Pablo Umana, Wollerau (CH)

(73) Assignee: ROCHE GLYCART AG, Schlieren (CH)

( * ) Notice: Subject to any disclaimer, the term of this patent is extended or adjusted under 35 U.S.C. 154(b) by 430 days.

(21) Appl. No.: 14/352,411

(22) PCT Filed: Oct. 16, 2012

(86) PCT No.: PCT/EP2012/070439
§ 371 (c)(1),
(2) Date: Apr. 17, 2014

(87) PCT Pub. No.: WO2013/057078
PCT Pub. Date: Apr. 25, 2013

(65) Prior Publication Data
US 2014/0255399 A1 Sep. 11, 2014

(30) Foreign Application Priority Data
Oct. 19, 2011 (EP) .................................. 11185798

(51) Int. Cl.
| | |
|---|---|
| C07K 1/22 | (2006.01) |
| C07K 14/735 | (2006.01) |
| G01N 33/53 | (2006.01) |
| C07K 16/00 | (2006.01) |
| C07K 16/06 | (2006.01) |

(52) U.S. Cl.
CPC .......... *C07K 1/22* (2013.01); *C07K 14/70535* (2013.01); *C07K 16/00* (2013.01); *C07K 16/065* (2013.01); *G01N 33/53* (2013.01); *C07K 2317/21* (2013.01); *C07K 2317/41* (2013.01)

(58) Field of Classification Search
None
See application file for complete search history.

(56) References Cited

U.S. PATENT DOCUMENTS

2007/0072307 A1* 3/2007 Godavarti ............ C07K 16/065
436/518
2013/0084648 A1* 4/2013 Bolton ..................... C07K 1/22
436/501

FOREIGN PATENT DOCUMENTS

WO 2010/048313 4/2010

OTHER PUBLICATIONS

Cartron et al. "Therapeutic activity of humanized anti-CD20 monoclonal antibody and polymorphism in IgG Fc receptor FcγRIIIa gene" Blood, 99(3), Feb. 1, 2002, pp. 754-758.*
Shields et al. "Lack of fucose on human IgG1 N-linked oligosaccharide improves binding to human FcγRIII and antibody-dependent cellular toxicity" J. Biological Chemistry, 277(3), 2002, pp. 26733-26740.*
Lammler et al., "Isolation of immunoglobulin G by affiniity chromatography using an IgG Fc receptor protein from *Streptococcus dysgalactiae* coupled to a solid phase" Journal of Immunological Methods 124(1):131-135 (Nov. 13, 1989).
Niwa et al., "Enhancement of the antibody-dependent cellular cytotoxicity of low-fucose IgG1 is independent of FcgammaRIIIa functional polymorphism" Clinical Cancer Research 10(18, Pt. 1):6248-6255 (Sep. 15, 2004).
Tojo et al., "A chromatographic approach for elevating the antibody-dependent cellular cytotoxicity of antibody composites" Biological & Pharmaceutical Bulletin 32(9):1604-1608 (Sep. 2009).
Shields et al. et al., "Lack of Fucose on Human IgG1 N-Linked Oligosaccharide Improves Binding to Human FcγRIII and Antibody-dependent Cellular Toxicity" J Biol Chem 277(30):26733-26740 (Jul. 26, 2002).
Okazaki et al., "Fucose depletion from human IgG1 oligosaccharide enhances binding enthalpy and association rate between IgG1 and FcgammaRIIIa" J Mol Biol. 336(5):1239-1249 (Mar. 5, 2004).

* cited by examiner

*Primary Examiner* — Daniel E Kolker
*Assistant Examiner* — James L Rogers
(74) *Attorney, Agent, or Firm* — Rebecca J. Wais

(57) ABSTRACT

The present invention relates to a method for the separation of antibodies, specifically antibodies having different degrees of fucosylation. The method is based on binding affinity of antibodies to Fc receptors. The invention further relates to the use of Fc receptors for the separation of antibodies having different degrees of fucosylation.

21 Claims, 13 Drawing Sheets

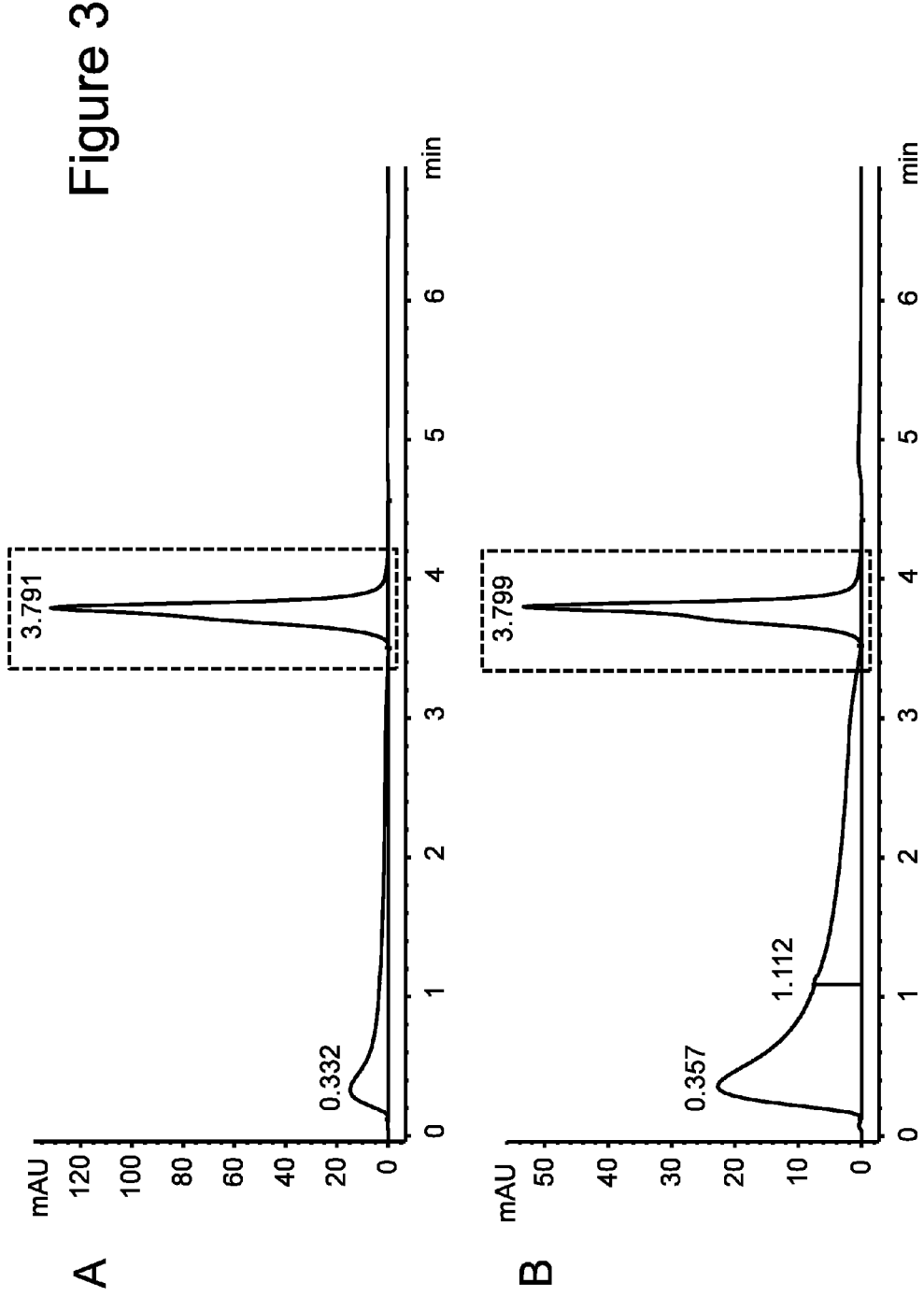

SEQUENCE LISTING

```
<160> NUMBER OF SEQ ID NOS: 2

<210> SEQ ID NO 1
<211> LENGTH: 222
<212> TYPE: PRT
<213> ORGANISM: Artificial Sequence
<220> FEATURE:
<223> OTHER INFORMATION: soluble FcgRIIIa(V158)-(Lys)6-(His)6 fusion
      protein

<400> SEQUENCE: 1

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
```

|     |     |     |     | 20  |     |     |     |     | 25  |     |     |     |     | 30  |
| --- | --- | --- | --- | --- | --- | --- | --- | --- | --- | --- | --- | --- | --- | --- |
| Gln | Trp | Tyr | Arg | Val | Leu | Glu | Lys | Asp | Ser | Val | Thr | Leu | Lys | Cys | Gln |
|     |     |     |     | 35  |     |     |     |     | 40  |     |     |     |     | 45  |     |
| Gly | Ala | Tyr | Ser | Pro | Glu | Asp | Asn | Ser | Thr | Gln | Trp | Phe | His | Asn | Glu |
|     |     |     |     | 50  |     |     |     |     | 55  |     |     |     |     | 60  |     |
| Ser | Leu | Ile | Ser | Ser | Gln | Ala | Ser | Ser | Tyr | Phe | Ile | Asp | Ala | Ala | Thr |
| 65  |     |     |     |     | 70  |     |     |     |     | 75  |     |     |     |     | 80  |
| Val | Asp | Asp | Ser | Gly | Glu | Tyr | Arg | Cys | Gln | Thr | Asn | Leu | Ser | Thr | Leu |
|     |     |     |     | 85  |     |     |     |     | 90  |     |     |     |     | 95  |     |
| Ser | Asp | Pro | Val | Gln | Leu | Glu | Val | His | Ile | Gly | Trp | Leu | Leu | Leu | Gln |
|     |     |     |     | 100 |     |     |     |     | 105 |     |     |     |     | 110 |     |
| Ala | Pro | Arg | Trp | Val | Phe | Lys | Glu | Glu | Asp | Pro | Ile | His | Leu | Arg | Cys |
|     |     |     |     | 115 |     |     |     |     | 120 |     |     |     |     | 125 |     |
| His | Ser | Trp | Lys | Asn | Thr | Ala | Leu | His | Lys | Val | Thr | Tyr | Leu | Gln | Asn |
|     |     |     |     | 130 |     |     |     |     | 135 |     |     |     |     | 140 |     |
| Gly | Lys | Gly | Arg | Lys | Tyr | Phe | His | His | Asn | Ser | Asp | Phe | Tyr | Ile | Pro |
| 145 |     |     |     |     | 150 |     |     |     |     | 155 |     |     |     |     | 160 |
| Lys | Ala | Thr | Leu | Lys | Asp | Ser | Gly | Ser | Tyr | Phe | Cys | Arg | Gly | Leu | Val |
|     |     |     |     | 165 |     |     |     |     | 170 |     |     |     |     | 175 |     |
| Gly | Ser | Lys | Asn | Val | Ser | Ser | Glu | Thr | Val | Asn | Ile | Thr | Ile | Thr | Gln |
|     |     |     |     | 180 |     |     |     |     | 185 |     |     |     |     | 190 |     |
| Gly | Leu | Ala | Val | Ser | Thr | Ile | Ser | Ser | Phe | Phe | Pro | Pro | Gly | Tyr | Gln |
|     |     |     |     | 195 |     |     |     |     | 200 |     |     |     |     | 205 |     |
| Gly | Lys | Lys | Lys | Lys | Lys | Lys | Gly | His | His | His | His | His | His |     |     |
|     |     |     |     | 210 |     |     |     |     | 215 |     |     |     |     | 220 |     |

<210> SEQ ID NO 2
<211> LENGTH: 669
<212> TYPE: DNA
<213> ORGANISM: Artificial Sequence
<220> FEATURE:
<223> OTHER INFORMATION: soluble FcgRIIIa(V158)-(Lys)6-(His)6 fusion
      protein, DNA

<400> SEQUENCE: 2

| atgtggcagc tgctcctccc aactgctctg ctacttctag tttcagctgg catgcggact | 60  |
| gaagatctcc caaaggctgt ggtgttcctg agcctcaat ggtacagggt gctcgagaag  | 120 |
| gacagtgtga ctctgaagtg ccagggagcc tactcccctg aggacaattc cacacagtgg | 180 |
| tttcacaatg agagcctcat ctcaagccag gcctcgagct acttcattga cgctgccaca | 240 |
| gtcgacgaca gtggagagta caggtgccag acaaacctct ccaccctcag tgacccggtg | 300 |
| cagctagaag tccatatcgg ctggctgttg ctccaggccc ctcggtgggt gttcaaggag | 360 |
| gaagacccta ttcacctgag gtgtcacagc tggaagaaca ctgctctgca taaggtcaca | 420 |
| tatttacaga atggcaaagg caggaagtat tttcatcata attctgactt ctacattcca | 480 |
| aaagccacac tcaaagacag cggctcctac ttctgcaggg ggcttgttgg gagtaaaaat | 540 |
| gtgtcttcag agactgtgaa catcaccatc actcaaggtt tggcagtgtc aaccatctca | 600 |
| tcattctttc cacctgggta ccaaggcaaa agaaaaaga aaagggcca ccaccatcac   | 660 |
| catcactga                                                        | 669 |

SEPARATION METHOD FOR FUCOSYLATED ANTIBODIES

This application is a 35 USC 371 of International Patent Application No. PCT/EP2012/070439 filed Oct. 16, 2012; which claims priority benefit to EP 11185798.3 filed Oct. 19, 2011, each of which are hereby incorporated herein by reference in their entireties.

SEQUENCE LISTING

The instant application contains a Sequence Listing submitted via EFS-Web and hereby incorporated by reference in its entirety. Said ACSII copy, created on Apr. 14, 2014, is named P4772-US_Sequence_Listing.txt, and is 3,429 bytes in size.

FIELD OF THE INVENTION

The present invention relates to a method for the separation of antibodies, specifically antibodies having different degrees of fucosylation. The method is based on binding affinity of antibodies to Fc receptors. The invention further relates to the use of Fc receptors for the separation of antibodies having different degrees of fucosylation.

BACKGROUND

Human $IgG_1$ consists of two Fab (fragment antigen binding) fragments, which comprise the variable regions responsible for antigen recognition, and a constant Fc (fragment crystallizable) domain, which interacts with components of the immune system and mediates immune effector functions such as antibody-dependent cell-mediated cytotoxicity (ADCC) and complement-dependent cytotoxicity (CDC). Carbohydrate structures attached to the conserved N-glycosylation site at asparagine 297 (Asn297, N297) within the CH2 domain of the constant region are mandatory for mediating these effector functions (1-4).

Naturally, the oligosaccharides attached to the Fc domain are predominantly biantennary complex-type structures varying in their content of bisecting GlcNAc (N-acetylglucosamine), terminal galactoses, core fucose and sialic acids (FIG. 1).

Recent studies have shown that modification of the carbohydrate composition strongly affects the antibody-mediated immune effector functions (3-5). A low level of galactosylation positively affects complement activation, while the lack of core fucose results in higher binding affinity to FcγRIIIa and thereby enhances ADCC (5-7). Several approaches have been developed to manipulate the glycosylation profile and to generate therapeutic antibodies with improved biological functions (8-10).

For instance, glycoengineered antibodies produced in mammalian cells overexpressing β(1,4)-N-acetylglucosaminyltransferase (GnT) III and mannosidase (Man) II feature high proportions of bisected, non-fucosylated oligosaccharides and trigger an enhanced ADCC as a result of an up to 50-fold higher affinity for FcγRIIIa (9). However the carbohydrate modifications introduced by overexpression of GnT III, which inhibit the fucosylation reaction, lead to only partially non-fucosylated antibodies. As the Fc domain of an IgG molecule carries two N-linked glycosylation sites, the partial inhibition of the fucosylation reaction can result in a variable distribution of the fucose within an antibody pool. Such an antibody preparation might contain a mixture of molecules carrying one or two fucose residues, while some of them are completely non-fucosylated. Obviously, such different degrees of non-fucosylation influence the overall affinity to FcγRIIIa and result in different biological activity. Therefore, a detailed characterization of such an antibody pool is mandatory.

Since the difference in affinity to FcγRIIIa between fucosylated and non-fucosylated IgG is up to 50-fold, this interaction can be utilized to separate the differently fucosylated species in an antibody pool and characterize them independently.

Existing affinity chromatography matrices used for IgG purification cannot discriminate between different glycosylation patterns within the IgG pool, since the immobilized capture protein specifically binds the protein backbone of the antibody. For instance Protein A and Protein G are binding in the interface between the CH2 and CH3 domain of the Fc region, while other IgG specific proteins such as Protein L are recognizing the constant part of the kappa light chain (11-13).

To enrich proteins carrying specific glycan structures, lectin affinity chromatography has been employed, for example using the Aleuria aurantia lectin (AAL) which binds fucose-containing glycans (14). Alternatively, glycan-targeting antibodies recognizing a specific carbohydrate structure have been used, for example antibodies specific for the Lewis x antigen (15). While these methods may be suitable to enrich glycoproteins carrying a specific carbohydrate, they are of limited use for the enrichment of glycoproteins lacking a specific carbohydrate, such as non-fucosylated antibodies. Moreover, neither of these methods is specific for antibodies and thus would require rigorous purification of an antibody pool prior to its application to the affinity matrix, to avoid contamination by other proteins carrying the targeted glycan structure. Finally, these methods rely on specific lectins or antibodies which may be difficult to obtain, and have not successfully been used for preparative purposes.

Given their greatly increased potency in inducing immune effector function which is of interest for experimental as well as therapeutic purposes, it would be desirable to separate partially or fully non-fucosylated antibodies from fully fucosylated ones present in an antibody pool. The present invention provides a simple and efficient method to achieve such separation.

DESCRIPTION OF THE INVENTION

The present invention provides a separation method based on the ability of certain Fc receptors, such as FcRγIIIa, to discriminate between fucosylated and (partially or fully) non-fucosylated antibodies. The method uses immobilized Fc receptors to separate differently fucosylated antibodies from an antibody pool for analytical as well as preparative purposes. The method described herein can be applied analytically to characterize the carbohydrate composition of an antibody pool. As it allows screening of large sample numbers, the method can be used, for example, for selecting host cell clones producing glycoengineered antibodies with a high content of non-fucosylated oligosaccharides. Preparative application allows preparation of fully non-fucosylated or fully fucosylated antibody populations, the different FcγRIIIa binding properties and biological activity of which can be characterized.

In a first aspect, the present invention provides a method for the separation of antibodies having different degrees of fucosylation, comprising the steps of:

a) providing a population of antibodies,
    b) contacting said population of antibodies with an Fc receptor immobilized on a support,
    c) eluting the antibodies not specifically bound to said Fc receptor, and d) eluting the antibodies specifically bound to said Fc receptor.

In a particular embodiment, the antibodies are IgG antibodies, more particularly IgG$_1$ antibodies. In some embodiments, the antibodies comprise a human Fc region. In one embodiment, the antibodies are glycosylated antibodies. In a specific embodiment, the antibodies are glycoengineered to have an altered oligosaccharide structure in their Fc region. In an even more specific embodiment, the antibodies are glycoengineered to have an increased proportion of non-fucosylated oligosaccharides in their Fc region, as compared to a corresponding non-glycoengineered antibody. In one embodiment, the antibodies have been produced in a host cell engineered to have increased β(1,4)-N-acetylglucosaminyltransferase (GnT) III activity, as compared to a non-engineered host cell. In a more specific embodiment the host cell additionally is engineered to have increased α-mannosidase II (ManII) activity. Increased GnTIII activity typically results from introducing into the host cell one or more polynucleotides encoding for one or more polypeptides having GnTIII activity, i.e. polypeptides that are able to catalyze the addition of a N-acetylglucosamine (GlcNAc) residue in β-1,4 linkage to the β-linked mannoside of the trimannosyl core of N-linked oligosaccharides. This includes fusion polypeptides exhibiting enzymatic activity similar to, but not necessarily identical to, an activity of β(1,4)-N-acetylglucosaminyltransferase III, also known as β-1,4-mannosyl-glycoprotein 4-beta-N-acetylglucosaminyl-transferase (EC 2.4.1.144), according to the Nomenclature Committee of the International Union of Biochemistry and Molecular Biology (NC-IUBMB), as measured in a particular biological assay, with or without dose dependency. In certain embodiments the polypeptide having GnTIII activity is a fusion polypeptide comprising the catalytic domain of GnTIII and the Golgi localization domain of a heterologous Golgi resident polypeptide. Particularly, the Golgi localization domain is the localization domain of mannosidase II or GnTI, most particularly the localization domain of mannosidase II. Alternatively, the Golgi localization domain is selected from the group consisting of: the localization domain of mannosidase I, the localization domain of GnTII, and the localization domain of α1,6 core fucosyltransferase. A glycoengineering methodology that can be used for glycoengineering antibodies to have an increased proportion of non-fucosylated oligosaccharides in their Fc region has been described in Umana et al., Nat Biotechnol 17, 176-180 (1999); Ferrara et al., Biotechn Bioeng 93, 851-861 (2006), and PCT publication nos. WO 99/54342, WO 2004/065540 and WO 03/011878, the content of each of which is expressly incorporated herein by reference in its entirety.

In particular embodiments, the binding affinity of the Fc receptor for the antibodies depends on the degree of fucosylation of the antibodies. In a specific such embodiment, the binding affinity of the Fc receptor for the antibodies decreases with the degree of fucosylation of the antibodies. In one embodiment, particularly where the antibodies are IgG antibodies, the Fc receptor is an Fcγ receptor. In a particular embodiment, the Fc receptor is FcγRIIIa. In a more specific embodiment, the Fc receptor is FcγRIIIa (V158). In some embodiments, particularly where the antibodies comprise a human Fc region, the Fc receptor is human. In one embodiment, the Fc receptor is a recombinant Fc receptor (i.e. the Fc receptor is obtained by recombinant production).

In one embodiment, the support on which the Fc receptor is immobilized is a polymer matrix. The polymer matrix typically is in beaded form. In one embodiment, the polymer matrix is cross-linked agarose or a derivative thereof. In a specific embodiment, the polymer matrix is Sepharose® (cross-linked agarose, available from GE Healthcare, Uppsala, Sweden). In another embodiment, the polymer matrix is cross-linked poly(styrene-divinylbenzene). In a specific embodiment the polymer matrix is POROS® (cross-linked poly(styrene-divinylbenzene), available from Applied Biosystems, Foster City, USA). The Fc receptor can be immobilized on the support in various ways. A skilled person will easily be able to determine the appropriate immobilization method based on the properties of the support. For example, immobilization on a polymer matrix is typically achieved through a chemical reaction of the protein to be immobilized with functional groups (e.g. hydroxyl groups, aldehyde groups, epoxide groups) comprised in the matrix. Suitable polymer matrices, as well as coupling chemistries and protocols are well known in the art. Immobilization on two different supports is also described in the Examples hereinbelow. In one embodiment, the support is not a cell or a cell membrane. In certain embodiments, the method is a chromatographic method. In one such embodiment, the support is comprised in a chromatography column. In one such embodiment, the contacting of the antibody population with the Fc receptor is performed by passing the antibody population through the chromatography column.

In particular embodiments, the population of antibodies is purified. In certain embodiments, the population of antibodies is affinity purified, particularly affinity purified using Protein A or Protein G. Affinity purification can, for example, be performed as batch purification by incubating the antibody population with an affinity matrix, or as chromatographic purification by passing the antibody population mobile phase over an affinity matrix stationary phase. In one embodiment, the population of antibodies is purified by affinity chromatography. In a more specific embodiment, the population of antibodies is purified by Protein A or Protein G affinity chromatography, particularly Protein A affinity chromatography. In other embodiments, the antibody population is purified by size exclusion chromatography, or by a combination of affinity chromatography and size exclusion chromatography.

In one embodiment, the population of antibodies is provided in solution. In a more specific embodiment, the population of antibodies is provided in a buffered solution. In one embodiment, the buffered solution has a pH value of around 7.0 to around 8.5, particularly a pH value of around 8. In one embodiment, the buffered solution is a Tris buffered solution. In an even more specific embodiment the buffered solution is 10 mM Tris, 50 mM glycine, 100 mM NaCl, pH 8, or 20 mM Tris, 20 mM MOPS (3-(N-morpholino)propanesulfonic acid), 20 mM sodium citrate, 100 mM NaCl, pH 8. In some embodiments, the contacting of the antibody population with the Fc receptor is performed in a buffered solution. In a particular such embodiment, the buffered solution is the same as the buffered solution wherein the population of antibodies is provided. In one embodiment, the population of antibodies is purified by Protein A or Protein G affinity chromatography, particularly Protein A affinity chromatography, and the contacting with the Fc receptor is performed in the same buffered solution in which the population of antibodies is obtained after said affinity chromatography (including neutralization of the antibody solution after elution from Protein A). In particular embodiments, no intermediate step is required between purification of the antibody population and the contacting with the Fc receptor.

In some embodiments, the method further comprises the step of:

c1) washing the support.

In one embodiment, said washing comprises contacting the support with a buffered solution that allows specific binding of the antibodies to the Fc receptor to be maintained, followed by removing said buffered solution. In one embodiment, the buffered solution has a pH value of around 7.0 to around 8.5, particularly a pH value of around 8. In one embodiment, the buffered solution is a Tris buffered solution. In an even more specific embodiment the buffered solution is 10 mM Tris, 50 mM glycine, 100 mM NaCl, pH 8, or 20 mM Tris, 20 mM MOPS (3-(N-morpholino)propanesulfonic acid), 20 mM sodium citrate, 100 mM NaCl, pH 8. In one embodiment, said buffered solution is the same as the buffered solution wherein the antibodies are provided. In one embodiment, the same buffered solution is used for providing the (purified) population of antibodies therein (step a), for contacting the population of antibodies with the Fc receptor (step b), for eluting the antibodies not specifically bound to the receptor (step c), and for washing the support (step c1).

In a particular embodiment, the method allows the separation of antibody sub-populations wherein either the majority of antibodies comprise fucose residues in none, in one or in both of the two N-glycans of the antibody Fc region. In a further particular embodiment, the method allows the separation of antibodies having a degree of fucosylation of at least 90%, preferably of at least 95%, antibodies having a degree of fucosylation of less than 20%, preferably of less than 10%, and antibodies having a degree of fucosylation of about 10% to 75%, preferably of about 20% to 60%. In one embodiment, the method is suitable for the separation of an antibody sub-population essentially consisting of partially fucosylated and fully non-fucosylated antibodies. In one embodiment, the method is suitable for the separation of an antibody sub-population essentially consisting of antibodies comprising fucose residues in none or in one of the two N-glycans of the antibody Fc region. In one embodiment, the method is suitable for the separation of an antibody sub-population essentially free of antibodies comprising fucose residues in both of the two N-glycans of the antibody Fc region.

In certain embodiments, the method is for analytical purposes. In other embodiments, the method is for preparative purposes.

In certain embodiments, the method further comprises the step of:

e) collecting the eluted antibodies of step c) and/or step d).

In some embodiments, the method further comprises the step of:

f) using the collected antibodies for experimental or therapeutic purposes.

In one embodiment, the eluted antibodies are detected by measuring UV absorbance at a wavelength of 280 nm.

In one embodiment, the elution of step c) comprises separation of the antibodies remaining free in the antibody population after the contacting in step b). Where the support is comprised in a chromatography column and the contacting of the antibody population with the Fc receptor is performed by passing the antibody population through the chromatography column, the antibodies eluted in step c) are found in the flow through of the chromatography column. In one embodiment, the antibodies eluted in step c) are fully fucosylated antibodies. In a more specific embodiment, the antibodies eluted in step c) have a degree of fucosylation of at least 90%, preferably at least 95%. In one embodiment, the majority of the antibodies eluted in step c) comprise fucose residues in each of the two N-glycans of the antibody Fc region.

In particular embodiments, the elution of step d) comprises contacting the support with a buffered solution that interrupts the binding of antibodies to the Fc receptor. In one such embodiment, the buffered solution has a pH value in the range of about 3 to about 5, preferably in the range of about 4 to about 5. In one embodiment, the buffered solution is a Tris buffered solution. In one embodiment, the antibodies eluted in step d) are partially fucosylated and/or fully non-fucosylated antibodies. In a more specific embodiment, the antibodies eluted in step d) have a degree of fucosylation of less than 90%, preferably less than 75%, most preferably less than 60%. In one embodiment, the majority of the antibodies eluted in step d) comprise fucose residues either in one or in none of the two N-glycans of the antibody Fc region.

In a particular embodiment, the elution of step d) is performed at different pH values. In one embodiment, the pH values are in the range of about 3 to about 5, preferably in the range of about 4 to about 5. In a specific embodiment, the pH values comprise 4.6 and 4.2. In another particular embodiment, the elution of step d) allows the separation of partially fucosylated antibodies and fully non-fucosylated antibodies. In a more specific embodiment, the elution of step d) allows the separation of antibodies having a degree of fucosylation of less than 20%, preferably of less than 10%, and antibodies having a degree of fucosylation of about 10% to 75%, preferably of about 20% to 60%. In yet another particular embodiment, the elution of step d) allows the separation of antibody sub-populations wherein either the majority of the antibodies comprise fucose residues in one of the two N-glycans of the antibody Fc region, or the majority of antibodies comprise fucose residues in none of the two N-glycans of the antibody Fc region. In some embodiments, the elution of step d) is performed by sequentially contacting the support with a series of buffered solutions that interrupt the binding of antibodies having different degrees of fucosylation to the Fc receptor. In a specific such embodiment, the buffered solutions have different pH values. In one embodiment, the pH values are in the range of about 3 to about 5, preferably in the range of about 4 to about 5. In a specific embodiment, the pH values comprise 4.6 and 4.2. In one embodiment, the buffered solutions are Tris buffered solutions. In a more specific embodiment the buffered solutions are 10 mM Tris, 50 mM glycine, 100 mM NaCl, or 20 mM Tris, 20 mM MOPS (3-(N-morpholino) propanesulfonic acid), 20 mM sodium citrate, 100 mM NaCl, with different pH values.

In a further aspect, the invention encompasses the use of an Fc receptor in a method for the separation of antibodies having different degrees of fucosylation. In one aspect, the invention provides the use of an Fc receptor in a method of the invention as described herein. In one embodiment, the Fc receptor is an Fcγ receptor. In a particular embodiment, the Fc receptor is FcγRIIIa. In a more specific embodiment, the Fc receptor is FcγRIIIa(V158). In one embodiment the Fc receptor is human. In a further embodiment, the Fc receptor is a recombinant Fc receptor. In a particular embodiment, the Fc receptor is immobilized on a support. The support may incorporate any of the features, singly or in combination, described in the preceding paragraphs in relation to the support used in the method of the invention.

In yet another aspect, the invention provides an Fc receptor immobilized on a support for use in a method for the separation of antibodies having different degrees of fucosylation, such as the method of the invention. In one embodiment, the Fc receptor is an Fcγ receptor. In a particular embodiment, the Fc receptor is FcγRIIIa. In a more specific embodiment, the Fc receptor is FcγRIIIa(V158). In one embodiment the Fc receptor is human. In a further embodiment, the Fc receptor is a recombinant Fc receptor. The support may incorporate any of the features, singly or in combination, described in the preceding paragraphs in relation to the support used in the method of the invention.

Terms are used herein as generally used in the art, unless otherwise defined in the following.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they comprise an Fc region or a region equivalent to the Fc region of an immunoglobulin. The term also encompasses fusion proteins comprising an Fc region or a region equivalent to the Fc region of an immunoglobulin.

The term "immunoglobulin" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by a hinge region (HR) and three constant domains (CH1, CH2, and CH3), also called a heavy chain constant region. In case of an IgE class immunoglobulin the heavy chain additionally has a CH4 domain. Hence, an immunoglobulin heavy chain is a polypeptide consisting in N-terminal to C-terminal direction of the following domains: VH-CH1-HR-CH2-CH3-(CH4). Similarly, from N- to C-terminus, each light chain has a variable region (VL), also called a variable light domain or a light chain variable domain, followed by a constant light (CL) domain, also called a light chain constant region. Hence, an immunoglobulin light chain is a polypeptide consisting in N-terminal to C-terminal direction of the following domains: VL-CL. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\alpha_2$ (IgA$_2$). The light chain of an immunoglobulin may be assigned to one of two types, called kappa (κ) and lambda (λ), based on the amino acid sequence of its constant domain. An immunoglobulin essentially consists of two Fab fragments and an Fc region, linked via the immunoglobulin hinge region.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of antibodies are called α, δ, ε, γ, and μ, respectively.

The term "Fc region" or "Fc domain" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cell-mediated cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie et al., Science 247, 1306-10 (1990)).

The term "fucosylation" refers to the presence of fucose residues within the oligosaccharides attached to the peptide backbone of an antibody. Specifically, a fucosylated antibody comprises α(1,6)-linked fucose at the innermost N-acetylglucosamine (GlcNAc) residue in one or both of the N-linked oligosaccharides attached to the antibody Fc region, e.g. at position Asn 297 of the human IgG$_1$ Fc domain (EU numbering of Fc region residues). Asn297 may also be located about ±3 amino acids upstream or downstream of position 297, i.e. between positions 294 and 300, due to minor sequence variations in immunoglobulins.

The "degree of fucosylation" is the percentage of fucosylated oligosaccharides relative to all oligosaccharides identified in an N-glycosidase F treated antibody sample by MALDI TOF MS. In a sample of a "fully fucosylated antibody" essentially all oligosaccharides comprise fucose residues, i.e. are fucosylated. In one embodiment, a fully fucosylated antibody has a degree of fucosylation of at least 90%. Accordingly, an individual antibody in such a sample typically comprises fucose residues in each of the two N-linked oligosaccharides in the Fc region. Conversely, in a sample of a "fully non-fucosylated" antibody essentially none of the oligosaccharides are fucosylated, and an individual antibody in such a sample comprises fucose residues in neither of the two N-linked oligosaccharides in the Fc region. In one embodiment, a fully non-fucosylated antibody has a degree of fucosylation of less than 10%. In a sample of a "partially fucosylated antibody" only part of the oligosaccharides comprise fucose. An individual antibody in such a sample can comprise fucose residues in none, one or both of the N-linked oligosaccharides in the Fc region, provided that neither essentially all individual antibodies of the sample comprise fucose residues in none of the N-linked oligosaccharides in the Fc region, nor essentially all individual antibodies of the sample comprise fucose residues in both of the N-linked oligosaccharides in the Fc region. In one embodiment, a partially fucosylated antibody has a degree of fucosylation of about 10 to about 75%.

As used herein, the terms "glycoengineer, glycoengineered, glycoengineering" refer to any manipulation of the peptide backbone or the post-translational modifications of a naturally occurring or recombinant polypeptide or fragment thereof which alter the glycosylation pattern of the polypeptide. Glycoengineering includes modifications of the amino acid sequence, of the side chain group of individual amino acids, or of the oligosaccharide structures, as well as combinations of these approaches. Glycoengineering also includes metabolic engineering of the glycosylation machinery of a cell, including genetic manipulations of the oligosaccharide synthesis pathways to achieve altered glycosylation of glycoproteins expressed in the cell. Furthermore, glycoengineering includes the effects of mutations and cell environment on glycosylation. In one embodiment, a glycoengineered antibody results from an alteration in glycosyltransferase activity in the host cell producing said antibody. Glycosyltransferases include for example β(1,4)-N-acetylglucosaminyltransferase III (GnTIII), β(1,4)-galactosyltransferase (GalT), β(1,2)-N-acetylglucosaminyltransferase I (GnTI), β(1,2)-N-acetylglucosaminyltransferase II (GnTII) and α(1,6)-fucosyltransferase. In a particular embodiment, the glycoengineered antibody results from altered glucosaminyltransferase activity and/or fucosyltransferase activity in the host cell producing said antibody. An antibody with an increased proportion of non-fucosylated oligosaccharides in its Fc region can be obtained, for example, by producing an antibody in a host cell having increased β(1,4)-N-acetylglucosaminyltransferase III (GnTIII) activity, optionally additionally having increased mannosidase II (ManII) activity, or a host cell having decreased α(1,6) fucosyltransferase activity.

"FcγRIIIa (V158)" refers to the isoform of FcγRIIIa (also known as CD16a; see Uni Prot No. P08637, NCBI accession no. NP_000560 for the human protein) having a valine (V) residue at amino acid position 158. IgG binding by FcγRIIIa (V158) was shown to be better than binding by FcγRIIIa (F158) (17).

By "specifically bound" is meant that the binding is selective for the Fc receptor and can be discriminated from unwanted or non-specific interactions. The ability of an antibody to bind to an Fc receptor can be measured either through an enzyme-linked immunosorbent assay (ELISA) or other techniques familiar to one of skill in the art, e.g. surface plasmon resonance (SPR) as described herein.

"Binding affinity" refers to the strength of the sum total of non-covalent interactions between a single binding site of a molecule (e.g. a receptor) and its binding partner (e.g. a ligand). Unless indicated otherwise, as used herein, "binding affinity" refers to intrinsic binding affinity which reflects a 1:1 interaction between members of a binding pair (e.g., a receptor and its ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well-established methods known in the art, including those described herein. A particular method for measuring affinity is surface plasmon resonance (SPR).

The term "purified" when used in connection with an antibody population means that the antibody population is essentially free of unrelated, non-antibody proteins. Various methods for the purification of antibodies are known in the art, including high performance liquid chromatography, ion exchange chromatography, gel electrophoresis, affinity chromatography, size exclusion chromatography and the like. An "affinity purified" antibody population refers to an antibody population that has been purified using an affinity matrix to which the antibodies, but not unrelated, non-antibody proteins, specifically bind, for example an affinity matrix comprising Protein A or Protein G.

The term "buffered solution" as used herein refers to a solution having a defined pH value, typically comprising a buffering agent which stabilizes the pH of the solution. Buffering agents are well known in the art and include, for example, citrate salts, acetate salts, histidine salts, succinate salts, malate salts, phosphate salts, lactate salts or tris (hydroxymethyl)amino-methane (Tris).

"Majority" as used herein means more than 50%, preferably more than 60%, most preferably more than 70% of the total.

peak 1; black triangles: peak 2; black circles: peak 3; white squares (only shown in B): wild-type IgG "B" (not glycoengineered).

Figure 8:
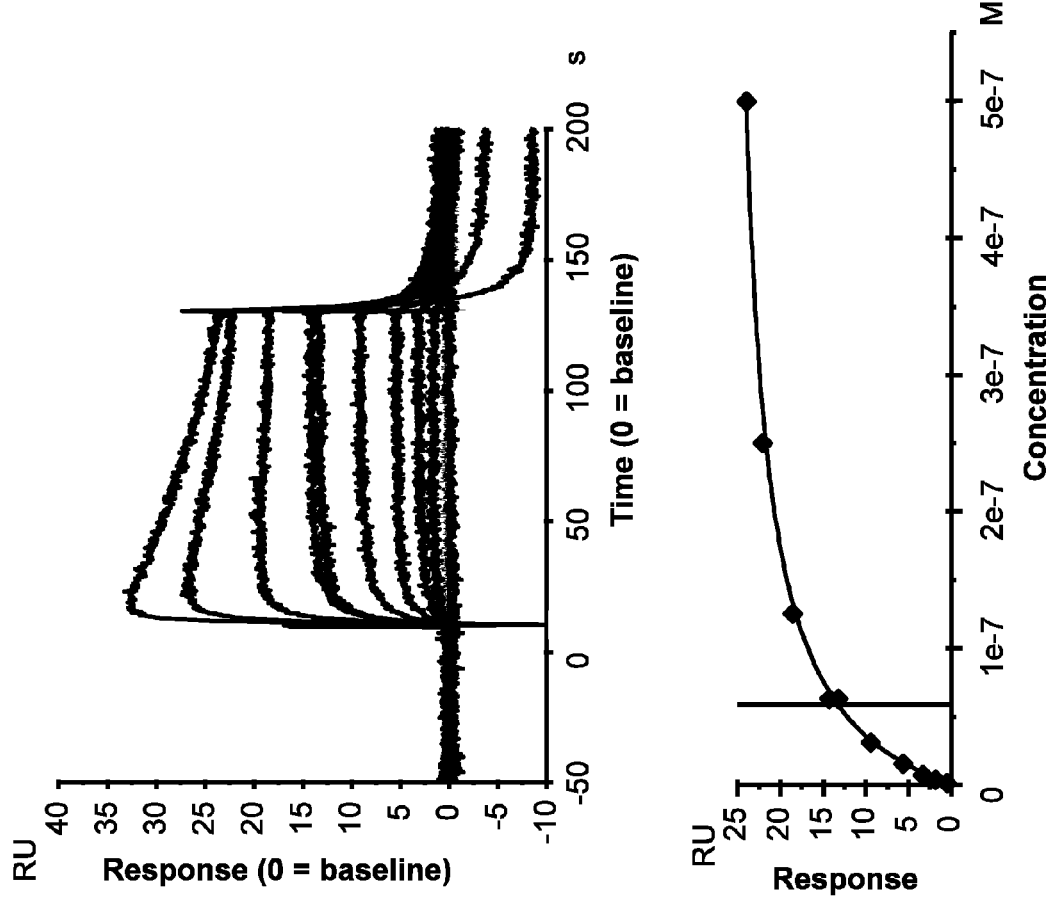
Figure 8:
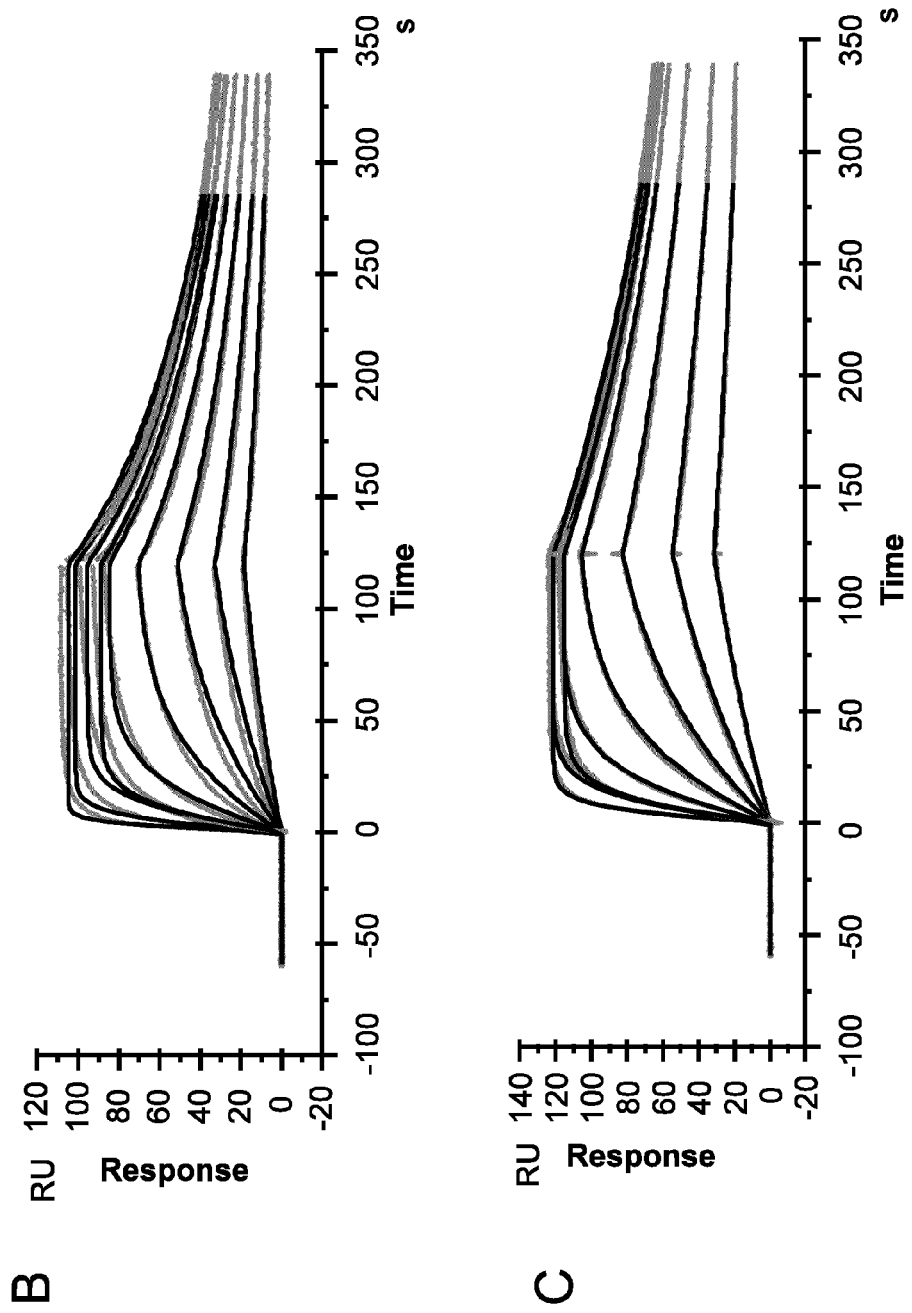
Figure 8:
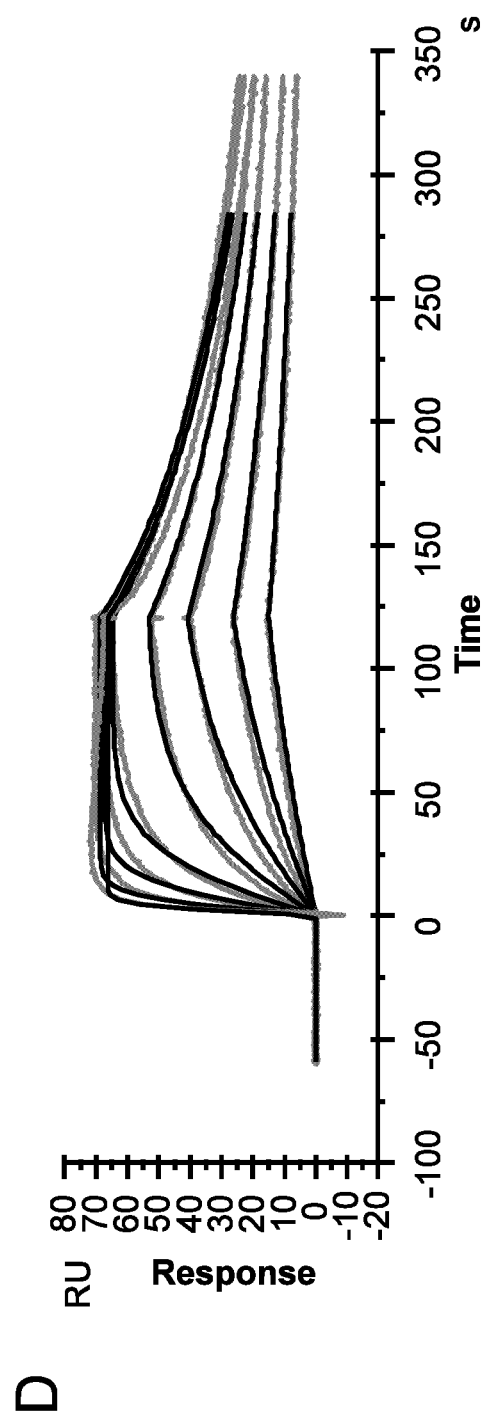
Figure 8:
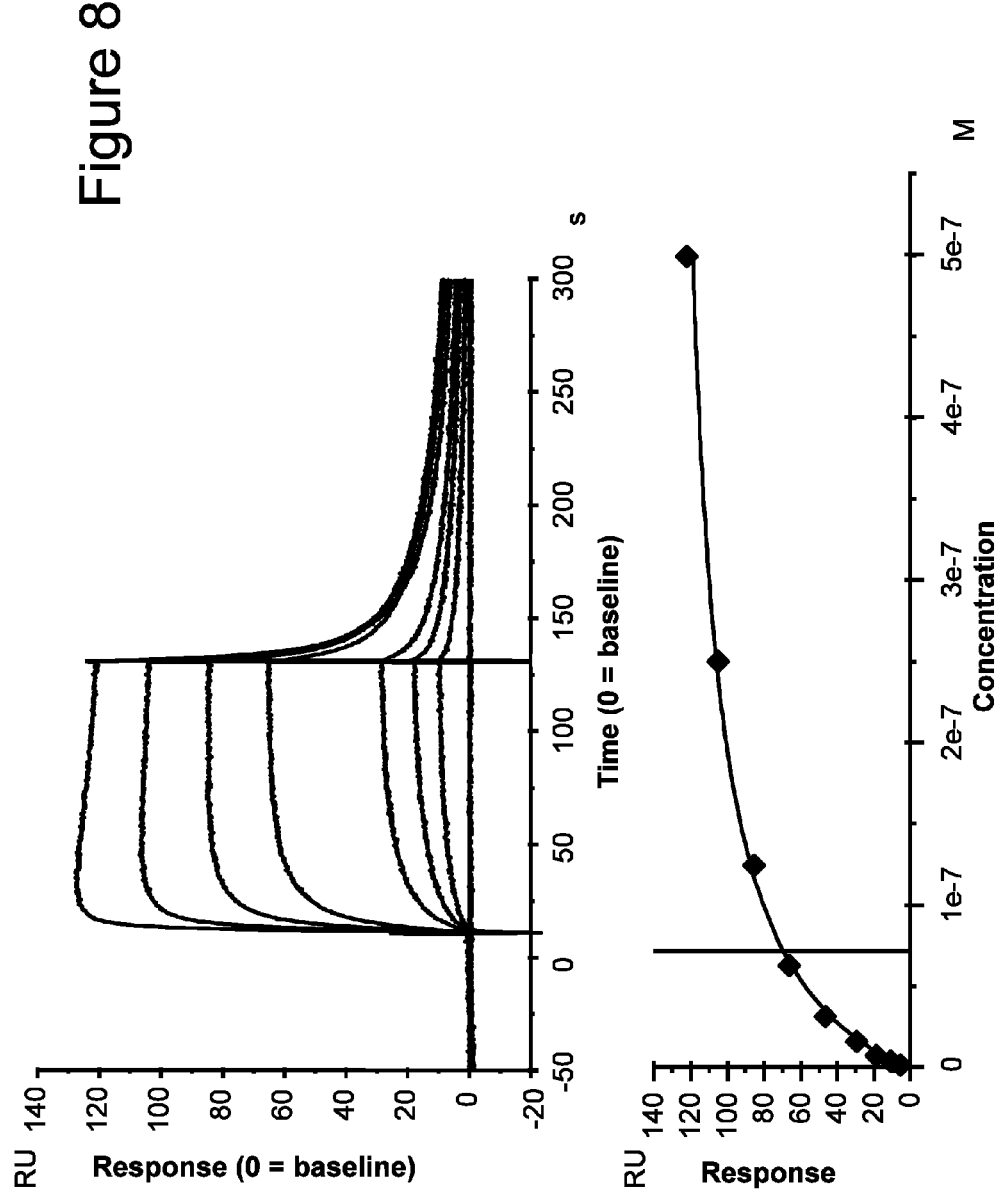

FIG. 8. Interaction of soluble human FcγRIIIa(V158) with antibody fractions collected from preparative FcγRIIIa (V158) chromatography, analyzed by surface plasmon resonance. Sensorgrams and fittings for A) IgG "B", peak 1 (analyzed in steady state); B) IgG "B", peak 2; C) IgG "B", peak 3; D) antibody pool of IgG "B" as loaded on FcγRIIIa (V158) column. E) Sensorgram of wild-type IgG "B" without glycoengineering (analyzed in steady state).

EXAMPLES

The following are examples of methods of the invention. It is understood that various other embodiments may be practiced, given the general description provided above.

Example 1

Production and Purification of Soluble Human FcγRIIIa(V158)$K_6H_6$

Soluble human FcγRIIIa (V158) with C-terminal (Lysine)$_6$ and (Histidine)$_6$ tags (see SEQ ID NOs 1 and 2) was produced by transfecting HEK293-EBNA cells with the mammalian expression vector using calcium phosphate transfection.

For transfection cells were grown as adherent monolayer cultures in T-flasks using DMEM culture medium supplemented with 10% (v/v) FCS, and transfected when they were between 50 and 80% confluent. For the transfection of a T150 flask, 15 million cells were seeded 24 hours before transfection in 25 ml DMEM culture medium supplemented with FCS (at 10% v/v final), and placed overnight at 37° C. in an incubator with a humidified 5% $CO_2$ atmosphere. For each T150 flask to be transfected a solution of DNA, $CaCl_2$ and water was prepared by mixing 94 µg total plasmid vector DNA in water to a final volume of 469 µl, and 469 µl of a 1 M $CaCl_2$ solution. To this solution, 938 µl of a 50 mM HEPES, 280 mM NaCl, 1.5 mM $Na_2HPO_4$ solution at pH 7.05 were added, mixed immediately for 10 s, and left to stand at room temperature for 20 s. The suspension was diluted with 10 ml of DMEM supplemented with 2% (v/v) FCS, and added to the T150 flask in place of the existing medium. Then additional 13 ml of transfection medium were added. The cells were incubated at 37° C., 5% $CO_2$ for about 17 to 20 hours, before medium was replaced by 25 ml DMEM, 10% FCS. The conditioned culture medium was harvested approx. 7 days post-media exchange by centrifugation for 15 min at 210×g, the solution was sterile filtered (0.22 µm filter) and sodium azide in a final concentration of 0.01% (w/v) was added, and kept at 4° C.

Figure 1:
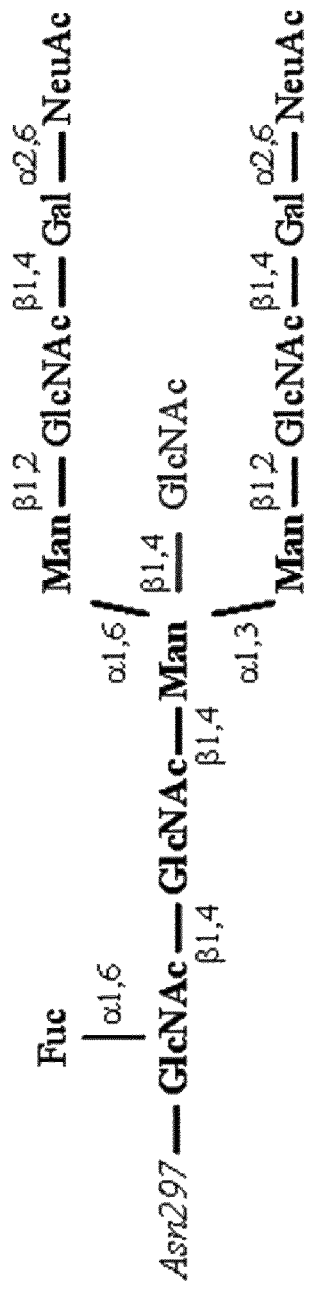
FIG. 1. N-linked oligosaccharide attached to Asn297 of the human IgG1 Fc domain. The sugars in bold define the pentasaccharide core, the addition of the other sugar residues is variable. GlcNAc: N-acetylglucosamine; Fuc: fucose; Man: mannose; Gal: galactose; NeuAc: N-acetylneuraminic acid.
Figure 2:
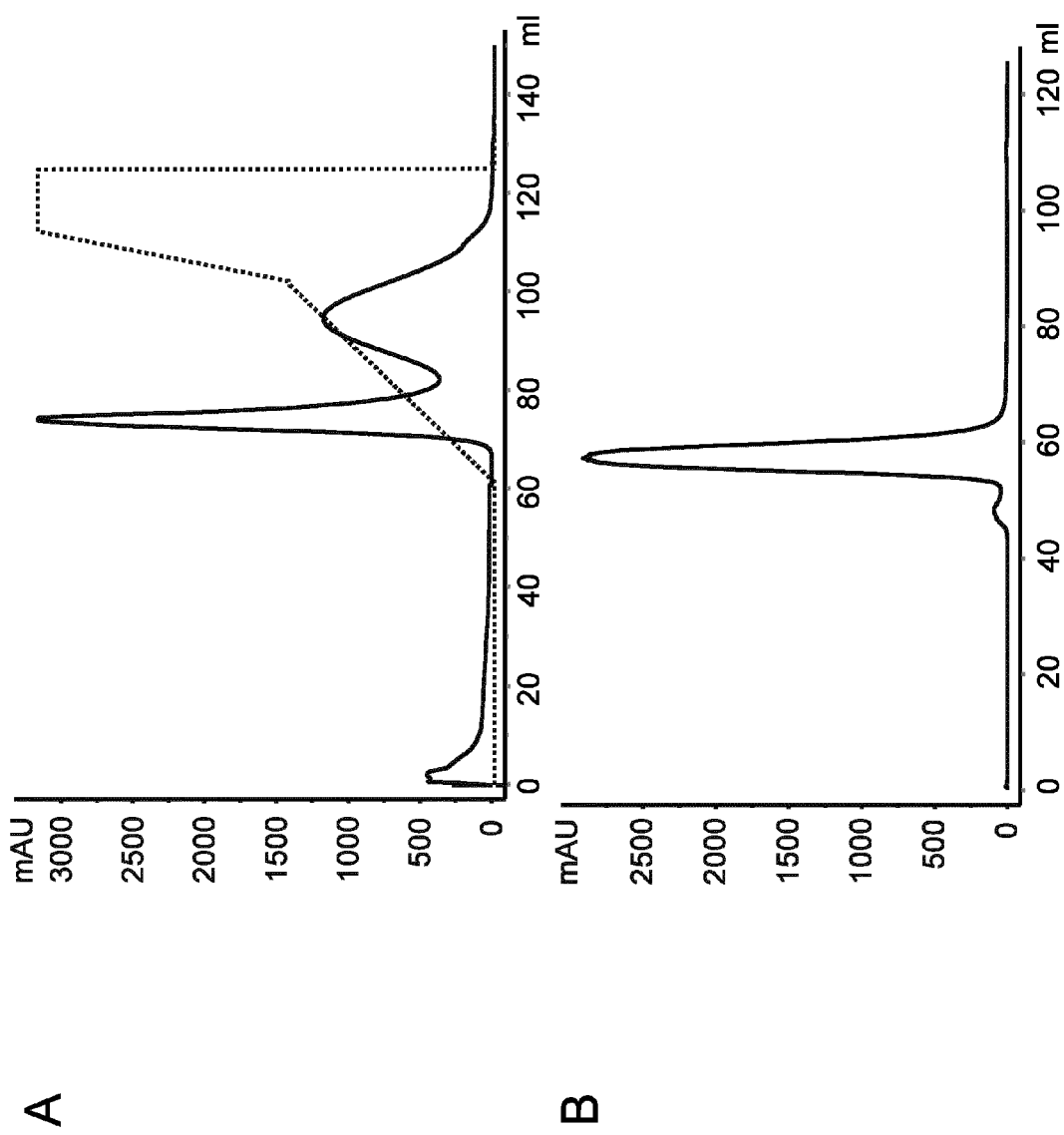
FIG. 2. Purification of soluble human FcγRIIIa(V158). A) Chromatogram of immobilized metal chelate chromatography (IMAC). Solid line: $A_{280nm}$; dotted line: gradient. B) Chromatogram of the size exclusion chromatography (SEC). Solid line: $A_{280nm}$. C) SDS PAGE, Coomassie-stained. Lane 1: molecular weight marker [kDa]; lane 2: FcγRIIIa(V158) reduced. D) Analytical SEC chromatogram ($A_{280nm}$). 50 µg sample were injected.
Figure 2:
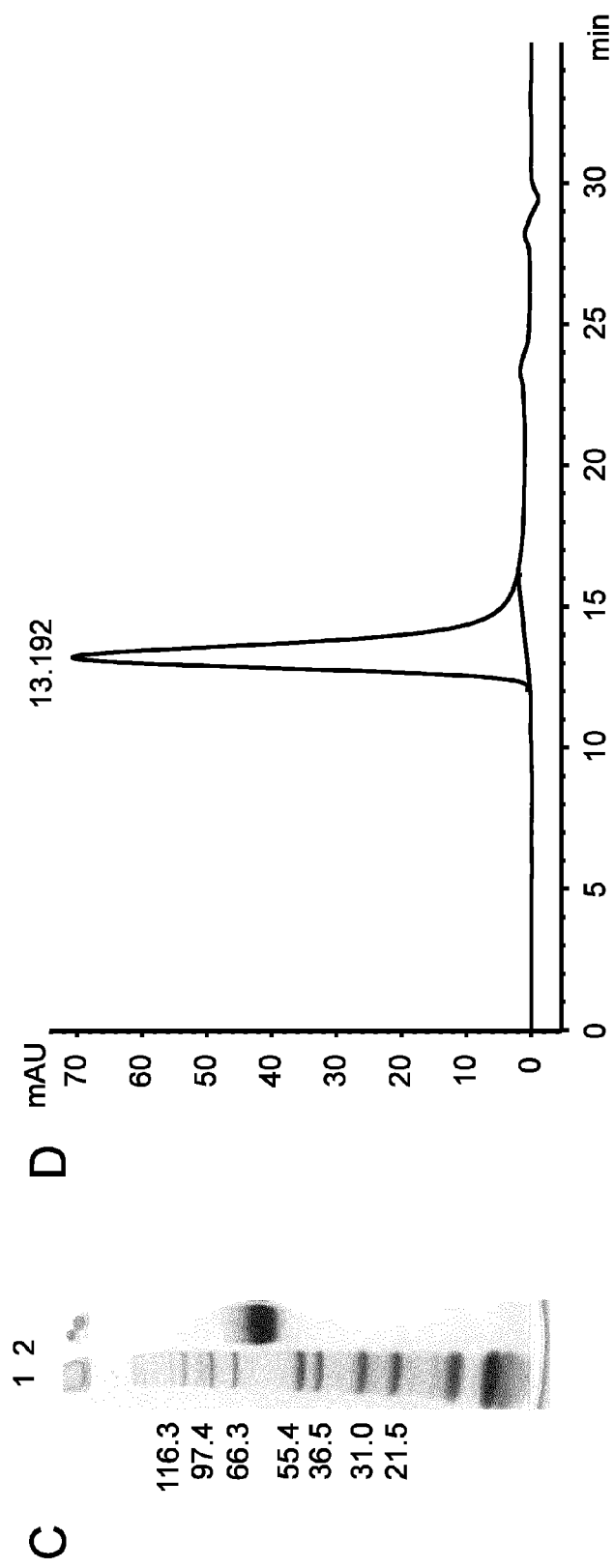

The secreted protein was purified by immobilized metal chelate chromatography (IMAC) followed by size exclusion chromatography (FIG. 2A, B).

For the metal chelate chromatography the supernatant was loaded on a NiNTA Superflow cartridge (column volume: 5 ml; Qiagen, Germany) equilibrated with buffer A (20 mM $Na_2HPO_4$ 0.5 M NaCl pH 7.4) at 4 ml/min. Unbound protein was removed by washing with at least 10 column volumes buffer A. FcγRIIIa(V158) was eluted with a gradient to buffer B (20 mM $Na_2HPO_4$, 0.5 M NaCl, 0.5 M imidazole, pH 7.4). The gradient consisted of three steps: 1) 0 to 45% buffer B over 8 column volumes, 2) 45 to 100% buffer B over 2 column volumes, and 3) 100% buffer B for 2 column volumes. The second eluting peak was pooled and concentrated using a centrifugal filter unit (Amicon Ultra MWCO 10 kD; Millipore, USA) before loading on the size exclusion chromatography column (HiLoad 16/60 Superdex 75; GE Healthcare, Sweden) equilibrated with 2 mM MOPS, 150 mM NaCl, 0.02% (w/v) $NaN_3$, pH 7.4.

The protein concentration of the purified protein sample was determined by measuring the optical density (OD) at 280 nm, using the molar extinction coefficient calculated on the basis of the amino acid sequence. Purity and molecular weight of recombinant human FcγRIIIa(V158) was analyzed by SDS PAGE in the presence and absence of a reducing agent (5 mM 1,4-dithiotreitol) and staining with Coomassie (InstantBlue™ from Expedeon). The NuPAGE® Pre-Cast gel system (4-12% Bis-Tris, Invitrogen, USA) was used according to the manufacturer's instruction (FIG. 2C). The aggregate content of the protein (50 µg sample) was analyzed using a Superdex 75 10/300GL analytical size exclusion column (GE Healthcare, Sweden) in 2 mM MOPS, 150 mM NaCl, 0.02% (w/v) $NaN_3$, pH 7.3 running buffer at 25° C. (FIG. 2D).

Example 2

Analyses of Antibody Fucosylation

Generation of Fc Fragments from Human IgG.

The antibodies were incubated for 72 hours at 25° C. in 50 mM Tris pH 8.0, 150 mM NaCl with 0.42 U plasmin (Roche, Switzerland) per mg. Cleaved Fc fragments were separated from Fab-fragments using Protein A beads, GE Healthcare) washed with 50 mM Tris pH 8.0, 100 mM glycine, 150 mM NaCl. Fc fragments were eluted with 50 mM Tris pH 3.0, 100 mM glycine, 150 mM NaCl. The eluate was neutralized by adding 1:40 v/v 2 M Tris pH 8.0 and loaded on a size exclusion chromatography column (Superdex S200 10/300 GL, GE Healthcare). Samples were concentrated and buffer was exchanged to 20 mM Tris pH 8 (Amicon, Millipore).

Release of N-Linked Oligosaccharides from Human Fc Fragments.

Different enzymes were used for hydrolyzing the N-linked glycans from human Fc fragments. The N-linked oligosaccharides were cleaved from 1 mg of Fc fragment by incubation with 0.005 U recombinant PNGase F (QAbio, USA). For release of carbohydrates from Fc fragments using non tagged Endo S (Genovis, Sweden) and Endo H (QAbio, USA), samples were incubated in a molar ratio of 1:20 with Endo S in combination with 0.1 U/mg Endo H. All reactions were incubated in 20 mM Tris pH 8.0 at 37° C. for 16 hours.

Release of N-Linked Oligosaccharides from Entire Human IgG.

For release of carbohydrates from entire human IgG using non tagged Endo S and Endo H, samples were buffer exchanged in 20 mM Tris pH 8.0 (Amicon 5.000 MWCO, Millipore) and incubated in a molar ratio of 1:7 with Endo S combined with 0.1 U/mg Endo H at 37° C. for 16 hours.

Carboxypeptidase B Treatment.

To remove heterogeneity caused by C-terminal lysine, samples were further incubated with Carboxypeptidase B (Roche; 1 mg/ml). Therefore 1 µl Carboxypeptidase B per 50 µg protein was added to the endoglycosidase reaction and incubated again for 1 hour at 37° C. After digestion the samples were purified using Protein A (POROS A 20, Applied Biosystems) and neutralized with 1:40 v/v 2 M Tris pH 8.0.

MALDI-TOF Mass Spectrometric Analysis.

Neutral oligosaccharide profiles for the human IgGs were analyzed by mass spectrometry (Autoflex, Bruker Daltonics GmbH) in positive ion mode according to Papac et al. (18).

ESI-MS Analysis of Glycan Structures from Human Fc Fragments by Direct Infusion (Off Line Detection).

20-50 μg (up to 90 μl) of antibody treated with the proteases plasmin and carboxypeptidase B and with endoglycosidases Endo S and Endo H were injected onto a Sephadex G25 self-packed ECO SR column (5×250 mm) (KronLab) equilibrated with 2% (v/v) formic acid, 40% (v/v) acetonitrile at a flow rate of 0.5 ml/min for 30 minutes. The injected antibody sample was desalted applying an 8 minute isocratic elution with 2% (v/v) formic acid, 40% (v/v) acetonitrile at a flow rate of 1 ml/min. The elution of the desalted protein was recorded by UV at 280 nm and the eluting sample (volume about 200-300 μl) was collected in a 1.5 ml reaction vial. An aliquot of the desalted sample was manually filled into a metal-coated glass needle (Proxeon Biosystems Nano ESI-needles, cat#ES387), inserted into the nanospray source of the mass spectrometry instrument and sprayed into an ESI-Q-TOF II mass spectrometer from Waters or into a Q-Star Elite mass spectrometer from Applied Biosystems. MS spectra were acquired using a capillary voltage of 1000 V, a cone voltage of 30 V in a mass range from 1000-2000 m/z in positive ion mode using a source temperature of 80° C. Desolvation temperature was off. MS data were acquired for 2-3 minutes by the respective instrument software. Molar masses of dimeric Fc fragments comprising different combinations of glycan structures truncated by the endoglycosidases applied (i.e molecules wherein both peptide chains carry only N-acetylglucosamine residues (GlcNAc/GlcNAc), molecules wherein one of the peptide chains additionally carries a fucose residue (GlcNAc+Fuc/GlcNAc), and molecules wherein both peptide chains carry fucose residues (GlcNAc+Fuc/GlcNAc+Fuc)) were determined from the respective m/z pattern of the Fc fragment species using an in-house developed software. The relative ratios of the three different residually glycosylated dimeric Fc-fragments were calculated with the same in-house software using the sum of peak areas of the m/z spectrum of a distinct glycosylation variant.

ESI-MS Analysis of Glycan Structures from Human Fc Fragments by LC/MS (on Line Detection).

The LC-MS method was performed on an Agilent Cap LC1100 coupled to a QT of II mass spectrometer (Waters). The chromatographic separation was performed on a Phenomenex Jupiter C18 column (5 μm particle size, 300 A pore size, 1×25 mm). Eluent A was 0.5% (v/v) formic acid in water, eluent B was 70% (v/v) isopropanol, 20% (v/v) acetonitrile, 9.5% (v/v) water and 0.5% (v/v) formic acid. The flow rate was 40 μl/min, the separation was performed at 75° C. using 2 μg protein in a final volume of 10 μl.

Example 3

Analytical FcγRIIIa Chromatography

Preparation of the Affinity Matrix.

10 mg FcγRIIIa(V158) were buffer exchanged into 0.1 M sodium phosphate, 0.05% (w/v) NaN$_3$, pH 7, using an centrifugal filter device (Amicon Ultra MWCO 10 kD; Millipore, USA) and concentrated to a final volume of 1.2 ml. Protein concentration was determined by UV spectroscopy measuring the optical density at 280 nm, and adjusted to 8 mg/ml. 440 μl POROS AL beads (Applied Biosystems, USA), corresponding to 0.14 g of dry beads, were added to the protein solution. Subsequently 41.5 μl of 1 M NaCNBH$_3$ in 0.01 M NaOH was added and the suspension incubated overnight at room temperature. The supernatant was removed by centrifugation of the beads and unbound protein was quantified by UV spectroscopy. The beads were quenched with 500 μl 1 M Tris, pH 7.4 and 23 μl 1 M NaCNBH$_3$ in 0.01 M NaOH for 30 min at room temperature. The beads were washed four times with 1 M NaCl and three times with 2 mM MOPS, 150 mM NaCl, 0.02% (w/v) NaN$_3$, pH 7.3. Finally 14 mg FcγRIIIa(V158) was coupled per g of POROS AL beads.

Analytical Chromatography Using FcγRIIIa(V158) Immobilized on POROS AL.

POROS AL beads with FcγRIIIa(V158) were packed in a 2×20 mm Upchurch Scientific column (column volume: 60 μl) which was mounted on the Agilent 1200 HPLC system (Agilent Technologies, USA). The buffers used were 10 mM Tris, 50 mM glycine, 100 mM NaCl, pH 8 to equilibrate and wash, or 10 mM Tris, 50 mM glycine, 100 mM NaCl, pH 3 to elute. The pump flow rate of the system was set to 0.5 ml/min. At time zero the antibody preparation (10 μg of Protein A-purified antibodies) was injected by the autosampler and washed for 2 min, then eluted in a step gradient of 0.66 minutes duration before re-equilibration for 4.33 minutes. The total cycle duration was 7 minutes.

Figure 3:
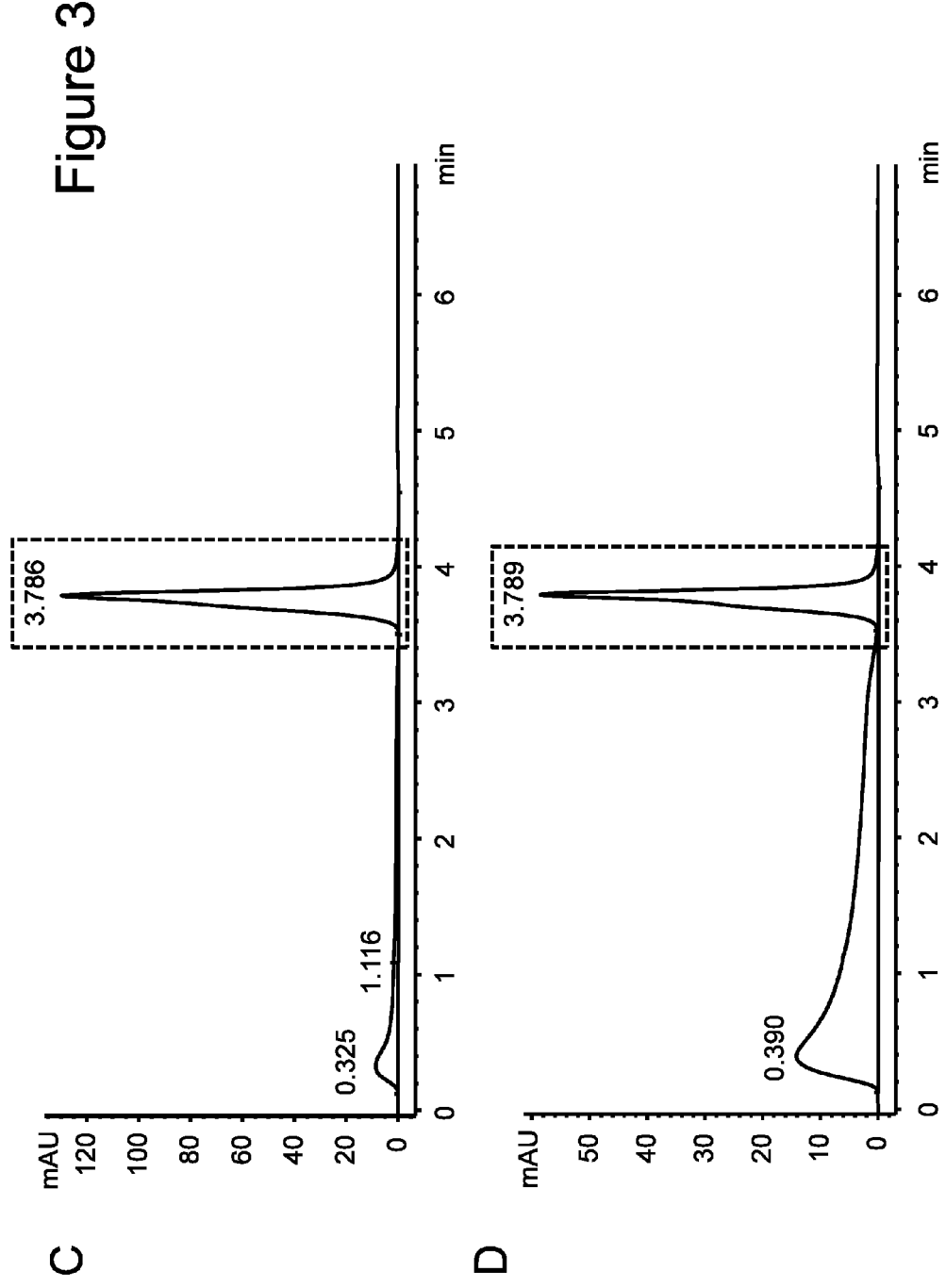
FIG. 3. Analytical FcγRIIIa(V158) chromatography. Chromatogram ($A_{280nm}$) for 10 µg of A) glycoengineered IgG "A"; B) wild-type IgG "A"; C) glycoengineered IgG "B"; D) wild-type IgG "B". The peak corresponding to the antibody fraction with high content of non-fucosylated glycans ("bound peak") is marked by a black square. The area of the "bound peak" is as follows: A) 66% of total peak area (48% non-fucosylation as determined by MALDI TOF MS); B) 26% of total peak area (10% non-fucosylation by MALDI TOF MS); C) 75% of total peak area (75% non-fucosylation by MALDI TOF MS); D) 31% of total peak area (9% non-fucosylation by MALDI TOF MS).

The chromatogram showed two peaks: the flow-through peak and the eluted peak (FIG. 3). The area of both peaks was determined by integration and the percentage of the eluted peak ("bound peak") relative to the total area was recorded.

To apply this method for high throughput analytical purposes and quantify the percentage of non-fucosylation in an antibody preparation the samples were first purified from supernatant via affinity chromatography using Protein A on the Agilent 1200 HPLC system and collected in a 96-well plate. The samples were eluted in 10 mM Tris, 50 mM glycine, 100 mM NaCl, pH 3, neutralized by adding 1:40 (v/v) 2 M Tris pH 8, and re-injected on the FcγRIIIa(V158) chromatography column. Since the antibody concentration was known after Protein A chromatography, the injection volumes were adapted to inject 10 μg of each sample on the FcγRIIIa(V158) chromatography column.

Figure 4:
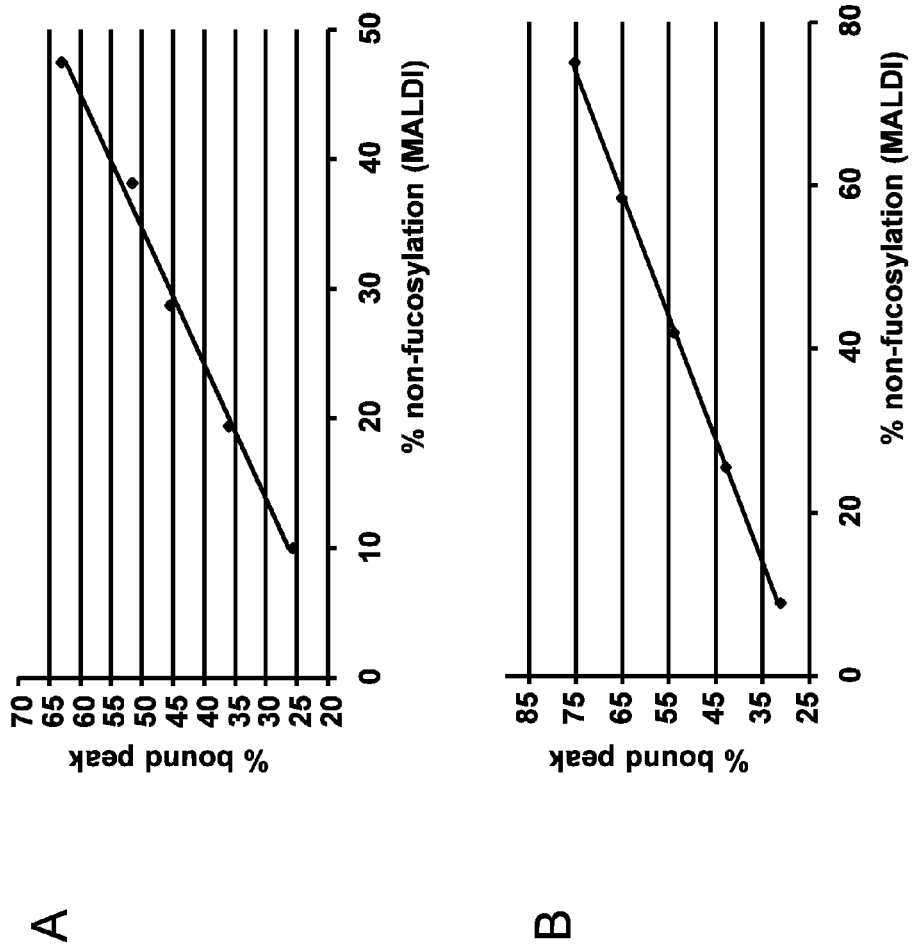
FIG. 4. Evaluation of analytical FcγRIIIa(V158) chromatography. Percentage of the area of the "bound peak" from FcgRIIIa(V158) chromatography column of the total peak area, in function of the percentage of non-fucosylation as determined by MALDI TOF MS. A) Mixtures of glycoengineered and wild-type IgG "A" (0-100% glycoengineered IgG). B) Mixtures of glycoengineered and wild-type IgG "B" (0-100% glycoengineered IgG).

Wild-type and glycoengineered antibodies were mixed in wash buffer to obtain different non-fucosylation ratios, and analyzed chromatographically directly on the FcγRIIIa (V158) column. The percentage of non-fucosylation determined by MALDI TOF MS and the percentage of the "bound peak" on the FcγRIIIa(V158) chromatography column show a linear correlation (FIG. 4).

Figure 5:
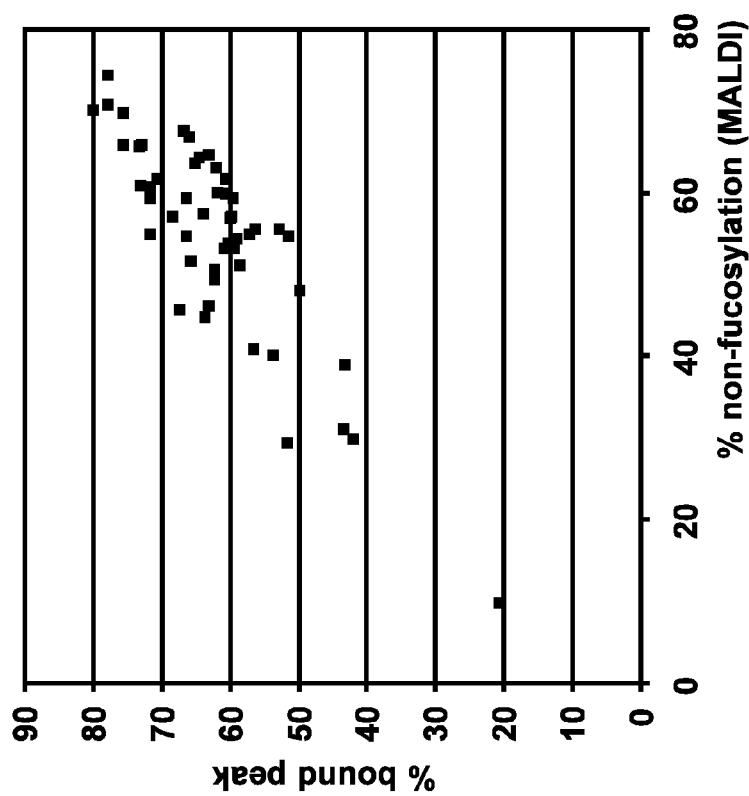
FIG. 5. Comparison of Protein A chromatography followed by MALDI TOF MS and Protein A chromatography with subsequent FcγRIIIa(V158) chromatography as two different methods to analyze the degree of fucosylation of antibodies purified from cell culture supernatant (glycoengineered IgG "C"). Percentage of the area of the "bound peak" from FcγRIIIa(V158) chromatography column of the total peak area in function of the percentage of non-fucosylation as determined by MALDI TOF MS.

Cell culture supernatant of different cell clones expressing the glycoengineered IgG "C" were analyzed in parallel by two different methods: 1) Protein A chromatography followed by MALDI TOF MS and 2) Protein A chromatography with subsequent FcγRIIIa(V158) chromatography. For this high-throughput analysis, 100 μl of supernatant was injected on the Protein A chromatography column, the eluate was neutralized by adding 1:40 (v/v) 2 M Tris pH 8, and either digested with PNGase F for MALDI TOF MS analysis of the carbohydrates or injected on the FcγRIIIa(V158) chromatography column. The advantage of the combination of Protein A chromatography with FcγRIIIa(V158) chromatography is that the 96-well plate containing the samples eluted from Protein A column can be used directly after neutralization without any additional buffer exchange or pipetting step. The percentage of the area of the "bound peak" on the FcγRIIIa(V158) column was compared to the percentage of non-fucosylation obtained by MALDI TOF MS for the antibodies produced by the different cell clones. A similar ranking was obtained with both methods, showing that the method of the invention allowed the identification of the clones producing the antibodies with the highest degree of non-fucosylation (FIG. 5).

These results show that FcγRIIIa chromatography can be used to screen cell culture supernatant in a high throughput manner and rank the produced antibodies according to their degree of non-fucosylation.

Example 4

Preparative FcγRIIIa Chromatography

Preparation of the Affinity Matrix.

30 mg FcγRIIIa(V158) were coupled to NHS activated Sepharose 4FF (GE Healthcare, Sweden). Briefly, FcγRIIIa (V158) was exchanged into 0.2 M $NaHCO_3$, 0.5 M NaCl, pH 8.2, concentrated to a final volume of 2 ml, and incubated for 4 hours at room temperature with 3 ml NHS activated beads that were previously washed with 1 mM cold HCl. The supernatant was removed and the beads were further incubated with 0.1 M Tris, pH 8.5 for 2 hours at room temperature. The beads were then packed into an empty Tricorn 5/150 column (GE Healthcare, Sweden) by gravity flow, followed by packing at 1.2 ml/min using an Äkta Explorer 10 (GE Healthcare, Sweden). Final column volume was 2.7 ml at a column length of 14 cm. 30 mg human FcγRIIIa(V158) were immobilized.

Preparative Separation of Antibodies with Different Degrees of Non Fucosylation Using FcγRIIIa(V158) Immobilized on NHS Sepharose 4 FF.

Figure 6:
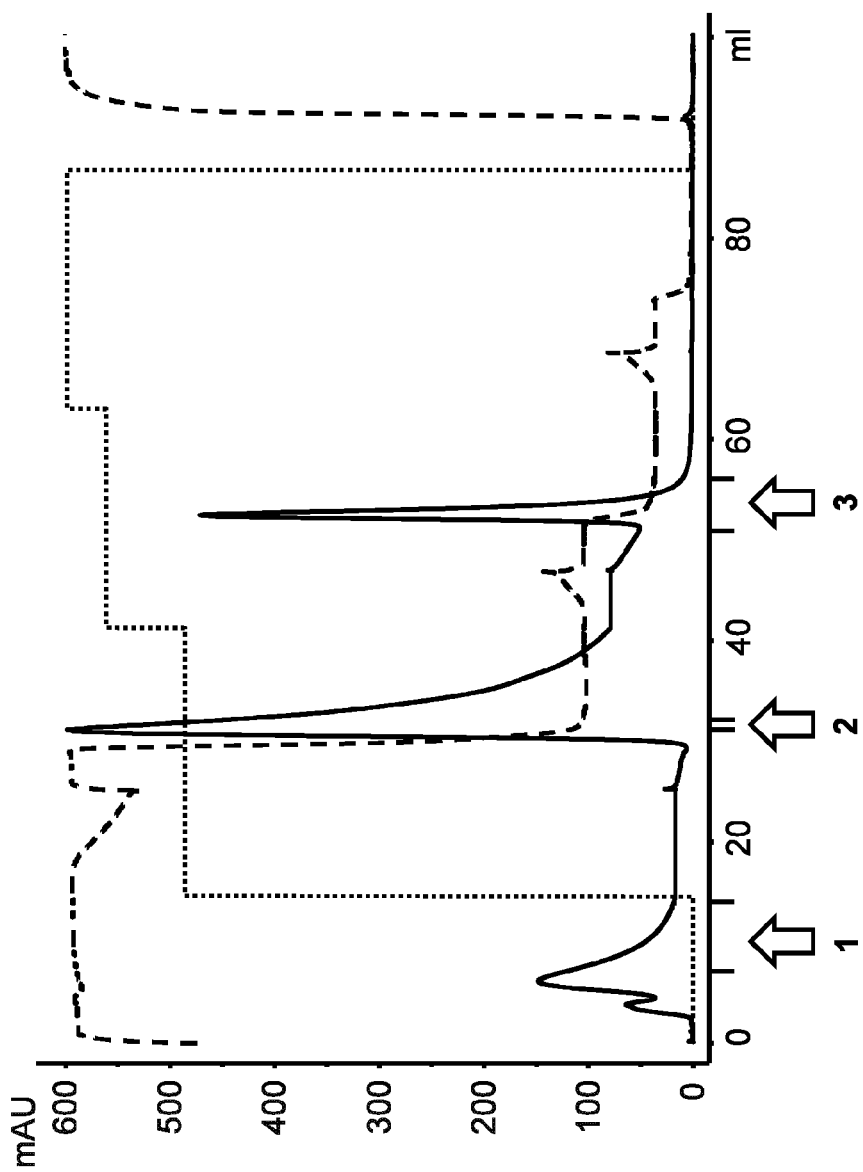
FIG. 6. Preparative FcγRIIIa(V158) chromatography. Chromatogram for glycoengineered IgG "A". IgG "A" elutes in three peaks: peak 1 is the flow-through of the column, peak 2 and 3 elute with two pH steps. The pools for peak 1, 2 and 3 are indicated. Solid line: $A_{280nm}$; dotted line: gradient; dashed line: pH-value.

For chromatography, the column was equilibrated with 10 column volumes 20 mM Tris, 20 mM MOPS, 20 mM sodium citrate, 100 mM NaCl, pH 8, and 3 mg of purified antibody (by Protein A affinity chromatography and size exclusion chromatography) was loaded at a flow rate of 0.1 ml/min. The column was washed with 20 mM Tris, 20 mM MOPS, 20 mM sodium citrate, 100 mM NaCl, pH 8 for 5 column volumes, and the different antibody populations were eluted with three pH steps at pH 4.6, pH 4.2 and pH 3 (FIG. 6). The desired pH values were obtained by mixing 20 mM Tris, 20 mM MOPS, 20 mM sodium citrate, 100 mM NaCl, pH 8 and 20 mM Tris, 20 mM MOPS, 20 mM sodium citrate, 100 mM NaCl, pH 3 at the appropriate ratios. The peaks were collected, concentrated and injected on Protein A HPLC for purification, or were batch purified with Protein A beads (required for subsequent MALDI TOF MS analysis). The antibodies were subsequently analyzed for their carbohydrate composition, their binding to the FcγRIIIa (V158), and their capacity to induce ADCC.

Example 5

Analysis of Separated Antibodies

Analysis of Carbohydrate Composition.

For MALDI TOF MS analysis of oligosaccharides, the oligosaccharides were cleaved off the purified antibodies with PNGase F and Endo H (16). The FcγRIIIa(V158) chromatography has separated fractions of antibodies with different content of non-fucosylated glycans. The first peak, corresponding to the flow-through, had the lowest amount of non-fucosylated oligosaccharides, followed by peaks two and three (see Table 2 and 3). MALDI TOF MS analysis, however, reveals only the overall amount of non-fucosylated oligosaccharides in a preparation.

To determine the distribution of fucose residues on the two antibody heavy chains in the Fc domain the samples were digested in a combinatory treatment using Endo S and Endo H (described above and in PCT publication no. WO 2011/039150, which is incorporated herein by reference in its entirety).

For the IgG "A" the purified antibodies were digested with plasmin, Endo H and Endo S to obtain Fc fragments carrying only the first N-acetylglucosamine residue of the oligosaccharide core and a fucose residue in case of fucosylated carbohydrates. These Fc fragments were analyzed by ESI-MS and the distribution of the fucose per Fc fragment was determined (Table 1).

TABLE 1

Content of non-fucosylated carbohydrates for antibody pool of IgG "A" separated in three fractions by FcγRIIIa(V158) chromatography. The degree of non-fucosylation was determined globally by MALDI TOF MS after PNGase F treatment (average from 7 runs) or the fucose distribution per Fc was determined by ESI-MS after plasmin/Endo S/Endo H digest (pool of 3 runs).

| Fractions | Average non-fucosylation* (MALDI-TOF MS) n = 7 | Standard error (MALDI-TOF MS) n = 7 | % Fc without fucose | % Fc with one fucose | % Fc with two fucoses | Average non-fucosylation* calculated[+] |
|---|---|---|---|---|---|---|
| IgG "A" peak 1 | 3.9% | 0.5% | 1% | 1% | 98% | 1.5% |
| IgG "A" peak 2 | 66.7% | 1.5% | 22% | 64% | 14% | 54% |
| IgG "A" peak 3 | 91.9% | 1.1% | 61% | 39% | 0% | 80% |
| IgG "A" start | 58.5% | 1.3% | 30% | 41% | 29% | 50% |

*Percentage of glycans lacking fucose residues of all glycans eluted in the respective peak.
[+]Calculated value for comparison of MALDI TOF and ESI-MS results. The value is calculated by adding percentages of glycans lacking fucose for all three Fc glycoforms. For example in peak 2, 22/100 of the Fc fragments comprise 2 non-fucosylated glycans (i.e. 44/200 glycans are non-fucosylated), 64/100 Fc fragments comprise 1 non-fucosylated glycan (i.e. 64/200 glycans are non-fucosylated) and 14/100 Fc fragments do not comprise any non-fucosylated glycans (i.e. 0/200 glycans are non-fucosylated), resulting in a total of 44 + 64 + 0 = 108/200 = 54% of non-fucosylated glycans eluted in peak 2.

For the IgG "B" the purified antibodies were digested with Endo H (QA Bio) and Endo S (Genovis) to obtain whole IgGs with glycans consisting of the first N-acetylglucosamine residue of the oligosaccharide core with or without fucose. These samples were analyzed by ESI-MS and the distribution of fucose per antibody was determined (Table 2).

TABLE 2

Content of non-fucosylated carbohydrates for antibody pool of IgG "B" separated in three fractions by FcγRIIIa(V158) chromatography. The degree of non-fucosylation was determined globally by MALDI-TOF MS after PNGase F treatment (average from 2 runs) or the fucose distribution per IgG was determined by ESI-MS after Endo S/Endo H digest (average from 2 runs).

| Fractions | Average non-fucosylation (MALDI-TOF MS) n = 2 | Standard error (MALDI-TOF MS) n = 2 | % Fc without fucose | % Fc with one fucose | % Fc with two fucoses | Average non-fucosylation* calculated[+] |
|---|---|---|---|---|---|---|
| IgG "B" peak 1 | 7.2% | 0.7% | 4.5% | 4.5% | 88% | 6.8% |
| IgG "B" peak 2 | 64.7% | 0.5% | 20.5% | 68.5% | 11% | 54.8% |
| IgG "B" peak 3 | 96.8% | 0.3% | 76.5% | 18.5% | 5% | 85.8% |
| IgG "B" start | 71.5% | 0% | 43% | 40% | 17% | 63% |

*Percentage of glycans lacking fucose residues of all glycans eluted in the respective peak.
[+]Calculated value for comparison of MALDI TOF and ESI-MS results. The value is calculated by adding percentages of glycans lacking fucose for all three Fc glycoforms. For example in peak 2, 20.5/100 of the Fc fragments comprise 2 non-fucosylated glycans (i.e. 41/200 glycans are non-fucosylated), 68.5/100 Fc fragments comprise 1 non-fucosylated glycan (i.e. 68.5/200 glycans are non-fucosylated) and 11/100 Fc fragments do not comprise any non-fucosylated glycans (i.e. 0/200 glycans are non-fucosylated), resulting in a total of 41 + 68.5 + 0 = 109.5/200 = 54.8% of non-fucosylated glycans eluted in peak 2.

For both IgG "A" and "B" peak 1 contained mostly antibodies carrying fucosylated sugars on both heavy chains in the Fc domain (i.e. fully fucosylated antibodies), whereas peak 2 contained mostly antibodies with one fucosylated and one non-fucosylated carbohydrate, and the population of peak 3 contains in majority completely non-fucosylated antibodies. The percentage of antibodies that are fully non-fucosylated appears to be slightly underestimated by the ESI-MS method, as the calculated value (see last column in Table 1 and 2 above) is generally lower than the MALDI TOF MS result.

Antibody-Dependent Cell-Mediated Cytotoxicity (ADCC).

The different fractions were tested for their capacity to induce ADCC. Raji (for the IgG "A" ADCC assay) or A549 (for the IgG "B" ADCC assay) cells were harvested (adherent cells with trypsin/EDTA), washed and labeled for 30 minutes at 37° C. with calcein (Invitrogen). After 30 minutes, cells were washed 3 times with AIM V medium and re-suspended in AIM V medium. They were plated in a round-bottom 96-well plate at a concentration of 30,000 cells/well. The respective antibody dilutions were added and incubated for 10 minutes before contact with human effector cells (NK92 1708 clone LC3 E11, which are NK92 cells transfected with FcγRIIIa(V158)). Effector and target cells at a ratio of 3:1 were co-incubated for 4 hours at 37° C. Lactate dehydrogenase (LDH) release was measured using the LDH Cytotoxicity detection Kit (Roche Applied Science, cat. no. 11 644 793 001). The calcein retention was determined by lysing the remaining cells with borate buffer (5 mM borate, 0.1% (v/v) Triton X-100) followed by measurement of the calcein fluorescence. For calculation of antibody-dependent killing, spontaneous release (only target and effector cells without antibody) was set to 0% killing and maximal release (target cells and 2% (v/v) Triton X-100) was set to 100% killing.

Figure 7:
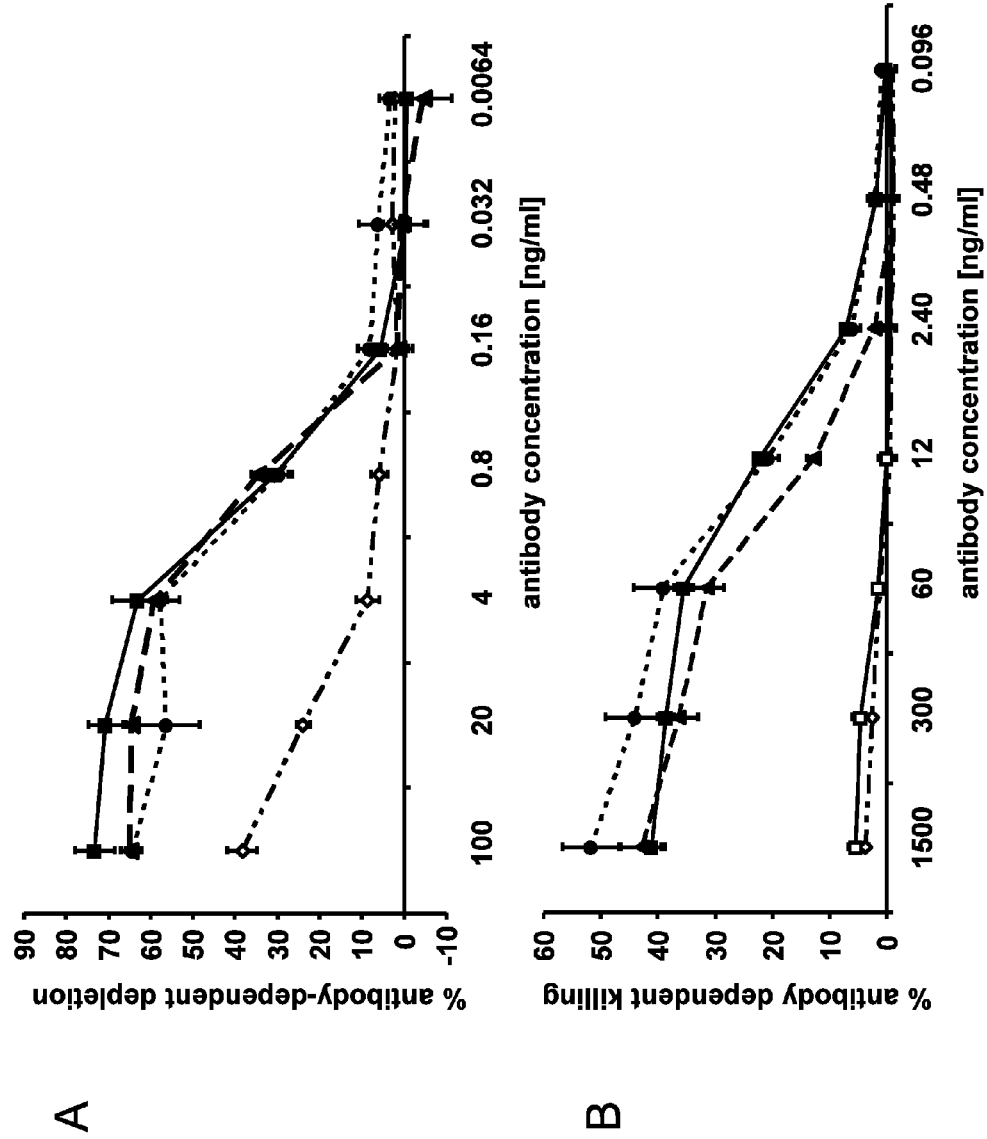
FIG. 7. Biological activity of antibody fractions collected from preparative FcγRIIIa(V158) chromatography. ADCC assays were performed for the 3 eluted peaks as well as the starting material (antibody pool as loaded on the FcγRIIIa (V158) column) for glycoengineered IgG "A" (A) and IgG "B" (B). Black squares: starting material; white diamonds.

Only the first peak (containing antibodies with fucosylated carbohydrates on both heavy chains) has a reduced capacity to induce ADCC, comparable to a wild-type IgG (FIG. 7). Both peaks 2 and 3 have a comparable ability to induce ADCC, showing that only one non-fucosylated glycan per antibody is enough to convey superior ADCC capability to an IgG.

FcγRIIIa Binding by Surface Plasmon Resonance.

Surface plasmon resonance was determined at 25° C. Human antigen "B" was immobilized by amine coupling on a CM5 chip following the manufacturer's instructions (GE Healthcare, Sweden). The IgG fractions were captured for 90 s at 100 nM and 10 µl/min. The human FcγRIIIa(V158) was passed at a concentration range from 1.95-500 nM with a flow rate of 50 µl/min through the flow cells for 120 s. The dissociation was monitored for 220 s. The surface was regenerated with two injections of 10 mM glycine, pH 2 for 60 s before the next injection. Bulk refractive index differences were corrected for by subtracting the response obtained on the reference flow cell. Association rates ($k_{on}$) and dissociation rates ($k_{off}$) were calculated using a simple one-to-one Langmuir binding model with RI=0 and Rmax=local (BIACORE® T100 Evaluation Software version 1.1.1) by simultaneously fitting the association and dissociation sensorgrams. The equilibrium dissociation constant ($K_D$) is calculated as the ratio $k_{off}/k_{on}$.

The results obtained by surface plasmon resonance were in accordance with the results of the ADCC assay (Table 3 and FIG. 8). The first peak as well as the wild-type IgG "B" had a $K_D$ around 50 nM with a very quick on and off rate, whereas the peak 2 and 3 as well as the glycoengineered IgG "B" had a $K_D$ around 3 nM for their binding to FcγRIIIa (V158) and a much slower off rate. The IgG of the peak 3 had the highest affinity for FcγRIIIa(V158).

TABLE 3

Affinity between FcγRIIIa (V158) and IgG "B". $K_D$ obtained by surface plasmon resonance at 25° C. The three peaks of the antibody pool of IgG "B" separated by FcγRIIIa (V158) chromatography and the starting material were captured on immobilized antigen and the FcgRIIIa (V158) was used as analyte.
Fitting: Kinetic (1:1 binding RI = 0, Rmax = local) or steady state.

| | Non-fucosylation (MALDI-TOF MS) | KD (nM) | Model | Sensorgram Figure 8 |
|---|---|---|---|---|
| IgG "B" peak 1 | 7.2% | 59 | Steady state | A |
| IgG "B" peak 2 | 64.7% | 3.7 | Kinetic | B |
| IgG "B" peak 3 | 96.8% | 1.8 | Kinetic | C |
| IgG "B" start (glycoengineered) | 71.5% | 2.5 | Kinetic | D |
| IgG "B" wild-type | 8% | 71 | Steady state | E |

Taken together, the examples show that the FcγRIIIa (V158) chromatography allows to separate antibodies according to their content of non-fucosylated carbohydrates in their Fc domain. The method can be applied to screen supernatant in a high-throughput manner (in combination with Protein A chromatography) to identify clones producing antibodies with a high degree of non-fucosylation or to separate fractions of an IgG according to its fucose content for further characterization. Analysis of antibody populations separated with FcγRIIIa(V158) chromatography showed for the first time that IgGs with either mostly one or two non-fucosylated carbohydrates in their Fc domain behave the same in terms of ADCC and that there is therefore no need for a 100% non-fucosylated antibody population to achieve enhanced effector function.

REFERENCES

1. Wright A, Morrison SL (1997) Effect of glycosylation on antibody function: implications for genetic engineering. Trends Biotechnol. 15(1):26-32
2. Krapp S et al (2003) Structural analysis of human IgG-Fc glycoforms reveals a correlation between glycosylation and structural integrity. J Mol Biol. 325(5):979-89
3. Raju T S (2008) Terminal sugars of Fc glycans influence antibody effector functions of IgGs. Curr Opin Immunol. 20(4):471-8
4. Jefferis R (2009) Recombinant antibody therapeutics: the impact of glycosylation on mechanisms of action. Trends Pharmacol Sci. 30(7):356-62
5. Hodoniczky J, Zheng Y Z, James D C (2005) Control of recombinant monoclonal antibody effector functions by Fc N-glycan remodeling in vitro. Biotechnol Prog. 21(6):1644-52
6. Malhotra R et al (1995) Glycosylation changes of IgG associated with rheumatoid arthritis can activate complement via the mannose-binding protein. Nat Med. 3:237-43
7. Shields R L et al (2002) Lack of fucose on human $IgG_1$ N-linked oligosaccharide improves binding to human FcγRIII and antibody-dependent cellular toxicity. J Biol Chem. 277(30):26733-40
8. Umana P et al (1999) Engineered glycoforms of an antineuroblastoma $IgG_1$ with optimized antibody-dependent cellular cytotoxic activity. Nat Biotechnol. 17(2):176-80
9. Ferrara C et al (2006) Modulation of therapeutic antibody effector functions by glycosylation engineering: influence of Golgi enzyme localization domain and co-expression of heterologous β(1,4)-N-acetylglucosaminyltransferase III and Golgi α-mannosidase II. Biotechnol Bioeng. 93(5):851-61
10. Kanda Y et al (2006) Comparison of biological activity among non-fucosylated therapeutic $IgG_1$ antibodies with three different N-linked Fc oligosaccharides: the high-mannose, hybrid, and complex types. Glycobiology. 17(1):104-18
11. Deisenhofer J et al (1978) Crystallization, crystal structure analysis and atomic model of the complex formed by a human Fc fragment and fragment B of protein A from *Staphylococcus aureus*. Hoppe Seylers Z Physiol Chem. 359(8):975-85
12. Groneborn A M and Clore G M (1993) Identification of the contact surface of a streptococcal protein G domain complexed with a human Fc fragment. J Mol Biol. 233(3):331-5
13. Graille M et al (2001) Complex between *Peptostreptococcus magnus* protein L and a human antibody reveals structural convergence in the interaction modes of Fab binding proteins. Structure. 9(8):679-87
14. Drake P et al (2011) A lectin affinity workflow targeting glycosite-specific, cancer-related carbohydrate structures in trypsin-digested human plasma. Anal Biochem. 408:71-85.
15. Cho W et al (2008) Use of glycan targeting antibodies to identify cancer-associated glycoproteins in plasma of breast cancer patients. Anal Chem. 80:5286-5292.
16. Schuster M et al (2005) Improved effector functions of a therapeutic monoclonal Lewis Y-specific antibody by glycoform engineering. Cancer Res. 65(17):7934-41.
17. Koene H R et al (1997) FcγRIIIa-158V/F polymorphism influences the binding of IgG by natural killer cell FcγRIIIa, independently of the FcγRIIIa-48L/R/H phenotype. Blood. 90:1109-1114.
18. Papac D I et al (1996) Analysis of acidic oligosaccharides and glycopeptides by matrix assisted laser desorption/ionization time-of-flight mass spectrometry. Anal Chem. 68:3215-3223.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method for the separation of antibodies having different degrees of fucosylation, comprising the steps of:
    (a) providing a population of antibodies,
    (b) contacting said population of antibodies with an Fc receptor immobilized on a support,
    (c) eluting the antibodies not specifically bound to said Fc receptor, and
    (d) eluting the antibodies specifically bound to said Fc receptor,
    wherein the Fc receptor is a FcγRIIIa(V158) having C-terminal (Lysine)$_6$ and (Histidine)$_6$ tags (SEQ ID NO:1).

2. The method of claim 1, wherein the binding affinity of the Fc receptor for the antibodies depends on the degree of fucosylation of the antibodies.

3. The method of claim 1, wherein the antibodies are IgG antibodies.

4. The method of claim 1, wherein the antibodies are glycoengineered to have an increased proportion of non-fucosylated oligosaccharides in their Fc region, as compared to a corresponding non-glycoengineered antibody.

5. The method of claim 1, wherein the population of antibodies is purified.

6. The method of claim 5, wherein the population of antibodies is affinity purified using Protein A or Protein G.

7. The method of claim 1, wherein the support is a polymer matrix.

8. The method of claim 1, wherein the support is comprised in a chromatography column.

9. The method of claim 1, further comprising the step of:
    c1) washing the support.

10. The method of claim 1, wherein the elution of step c) comprises separation of the antibodies remaining free in the antibody population after the contacting in step b).

11. The method of claim 1, wherein the antibodies eluted in step c) are fully fucosylated antibodies.

12. The method of claim 1, wherein the elution of step d) comprises contacting the support with a buffered solution that interrupts the binding of antibodies to the Fc receptor.

13. The method of claim 12, wherein the buffered solution has a pH value in the range of about 3 to about 5.

14. The method of claim 1, wherein the elution of step d) is performed at different pH values.

15. The method of claim 14, wherein the pH values comprise 4.6 and 4.2.

16. The method of claim 1, wherein the antibodies eluted in step d) are partially fucosylated and/or fully non-fucosylated antibodies.

17. The method of claim 1, wherein the method is for analytical purposes.

18. The method of claim 1, wherein the method is for preparative purposes.

19. The method of claim 1, further comprising the step of: collecting the eluted antibodies of step c) and/or step d).

20. The method of claim 19, further comprising the step of:
    using the collected antibodies for experimental or therapeutic purposes.

21. An Fc receptor immobilized on a support for use in the method of claim 1, wherein the Fc receptor is a FcγRIIIa (V158) receptor having C-terminal (Lysine)$_6$ and (Histidine)$_6$ tags (SEQ ID NO:1) and the support is a polymer matrix comprised in a chromatography column.

* * * * *